US010131933B2

(12) United States Patent
Stevens et al.

(10) Patent No.: US 10,131,933 B2
(45) Date of Patent: Nov. 20, 2018

(54) ASSAY FOR CLOSTRIDIUM BOTULINUM NEUROTOXIN

(75) Inventors: Gregory Stevens, Freiburg (DE); Michael Krueger, Emmendingen (DE); Andrea Zgaga-Griesz, Muellheim (DE); Gerald Urban, Freiburg (DE); Dalice Silver, Freiburg (DE)

(73) Assignee: Albert-Ludwigs-Universitaet Freiburg, Freiburg (DE)

( * ) Notice: Subject to any disclaimer, the term of this patent is extended or adjusted under 35 U.S.C. 154(b) by 0 days.

(21) Appl. No.: 14/349,737

(22) PCT Filed: Sep. 3, 2012

(86) PCT No.: PCT/EP2012/067100
§ 371 (c)(1),
(2), (4) Date: May 15, 2014

(87) PCT Pub. No.: WO2013/050204
PCT Pub. Date: Apr. 11, 2013

(65) Prior Publication Data
US 2014/0273039 A1   Sep. 18, 2014

(30) Foreign Application Priority Data

Oct. 5, 2011   (EP) .................................... 11184030

(51) Int. Cl.
*C12Q 1/66* (2006.01)
*C12Q 1/37* (2006.01)
*C12N 9/02* (2006.01)

(52) U.S. Cl.
CPC ............. *C12Q 1/66* (2013.01); *C12N 9/0069* (2013.01); *C12Q 1/37* (2013.01); *G01N 2333/33* (2013.01)

(58) Field of Classification Search
CPC .......... C12Q 1/66; C12Q 1/37; C12N 9/0069; G01N 2333/33
USPC ........................................................ 435/23
See application file for complete search history.

(56) References Cited

U.S. PATENT DOCUMENTS

| | | | | |
|---|---|---|---|---|
| 6,410,245 B1* | 6/2002 | Northrop | .................. | C07K 7/06 424/141.1 |
| 2003/0017450 A1* | 1/2003 | Oon | ....................... | C12Q 1/706 435/5 |
| 2005/0100973 A1* | 5/2005 | Steward | ............... | C07K 14/001 435/7.32 |
| 2011/0027910 A1* | 2/2011 | Weir | .................... | C07K 14/705 436/501 |

FOREIGN PATENT DOCUMENTS

WO    WO 2004/031355    4/2004

OTHER PUBLICATIONS

Tsai et al. Targeting Botulinum Neurotoxin Persistence by the Ubiquitin-Proteosome System; PNAS, vol. 107, No. 38 (2010) pp. 16554-16559.*
Davletov et al. Beyond Botox: Advantages and Limitations of Individual Botulinum Neurotoxins; Trends in Neurosciences, vol. 28, No. 8 (2005) pp. 446-452.*
Vaidyanathan et al. Proteolysis of Snap-25 Isoforms by Botulinum Neurotoxin Types A, C, and E: Domains and Amino Acid Residues Controlling the Formation of Enzyme-Substrate Complexes and Cleavage; Journal of Neurochemistry, vol. 72, pp. 327-337. (Year: 1999).*
Ruge, Daniel et al., *Analytical Biochemistry*, Apr. 2011, vol. 411, No. 2, pp. 200-209.
Homaei, A.A. et al., "Enzyme Immobilization: An Update", *J. Chem. Biol.* (2013) 6:185-205.
Knecht, S. et al, "Oligohis-tags: Mechanisms of Binding to Ni2+-NTA Surfaces", *J. Mol. Recognit.* (2009) 22: 270-279.
Nieba, L. et al, "BIACORE Analysis of Histidine-Tagged Proteins Using a Chelating NTA Sensor Chip", *Analytical Biochemistry* (1997) 252:217-228.
Sassolas, A. et al, "Immobilization Strategies to Develop Enzymatic Biosensors", *Biotechnology Advances* (2012) 30:489-511.
Van Oss, C. J. et al, "Nature of the Antigen-Antibody Interaction. Primary and Secondary Bonds: Optimal Conditions for Association and Dissociation", *J. Chromatography* (1986) 376: 111-119.
Walker, I. et al, "Mutations in Maltose-Binding Protein that Alter Affinity and Solubility Properties", *Appl. Microbiol. Biotechnol.* (2010) 88: 187-197.
Bornhorst, J.A. et al., "Purification of proteins using polyhistidine affinity tags", *Methods Enzymol* (2000), vol. 326: 245-54.
Knecht, S., et al., "Oligohis-tags: mechanisms of binding to Ni2+-NTA surfaces", *J. Mol. Recognit.* (2009), vol. 22: 270-279.
Lin, P.-C. et al., "Protein Biochips: Oriented Surface Immobilization of Proteins", *Macromol. Chem. Phys.* (2010), vol. 211: 136-144.
Rowinska-Zyrek, M. et al., "His-rich sequences—is plagiarism from nature a good idea?", *New J. Chem.* (2013), vol. 37: 58-70.
Talbert, J.N. et al. , "Enzymes on material surfaces", *Colloids Surfaces B Biointerfaces* (2012), vol. 93: 8-19.
Stevens, GB et al., "Bioluminescence assay for the highly sensitive detection of botulinum neurotoxin A activity", *Analyst* (2013), vol. 138 (20): p. 6154-62.
Dorner, M.B., Schulz, K.M., Kull, S., Dorner, B.G., (2012), "Complexity of Botulinum Neurotoxins: Challenges for Detection Technology", in: Rummel, A., Binz, T. (Eds.), *Botulinum Neurotoxins. Current Topics in Microbiology and Immunology.* pp. 219-255.

(Continued)

Primary Examiner — Julie Wu
Assistant Examiner — Paul C Martin
(74) *Attorney, Agent, or Firm* — Chalin A. Smith; Smith Patent, LLC

(57) ABSTRACT

The present invention relates to materials and methods suitable for determining the presence or amount of Botulinum toxin (BoNT) in a test sample by means of a luminescence assay in which the substrate peptide is composed of:
an amino acid sequence susceptible to proteolytic cleavage by BoNT,
an amino acid sequence corresponding to a reporter domain encoding a fluorescent or bioluminescent polypeptide, and
a tag suitable for attaching the substrate peptide to a suitable support, preferably by covalent bond.

19 Claims, 26 Drawing Sheets

Specification includes a Sequence Listing.

(56) References Cited

OTHER PUBLICATIONS

Khan, F., He, M., Taussig, M.J., (2006). "Double-Hexahistidine Tag with High-Affinity Binding for Protein Immobilization, Purification, and Detection on Ni-Nitrilotriacetic Acid Surfaces", *Anal. Chem.* 78, 3072-3079.

Stevens, G.B., Silver, D.A., Zgaga-Griesz, A., Krueger, M., Urban, G.A., 2011. "Rapid, Sensitive Detection of Clostridium Botulinum Neurotoxin in Blood Plasma", in: 48th Annual IBRCC Meeting. Santa Fe, New Mexico, USA. (Poster Abstract).

Stevens, G.B., Silver, D.A., van Oordt, T., Vashist, S.K., Urban, G.A., Krueger, M., 2012. "Optimizing the luciferase release assay for the automated detection of Botulunim Neurotoxin type A", in: 49th Annual IBRCC Meeting Baltimore, Maryland, USA. (Poster Abstract).

\* cited by examiner

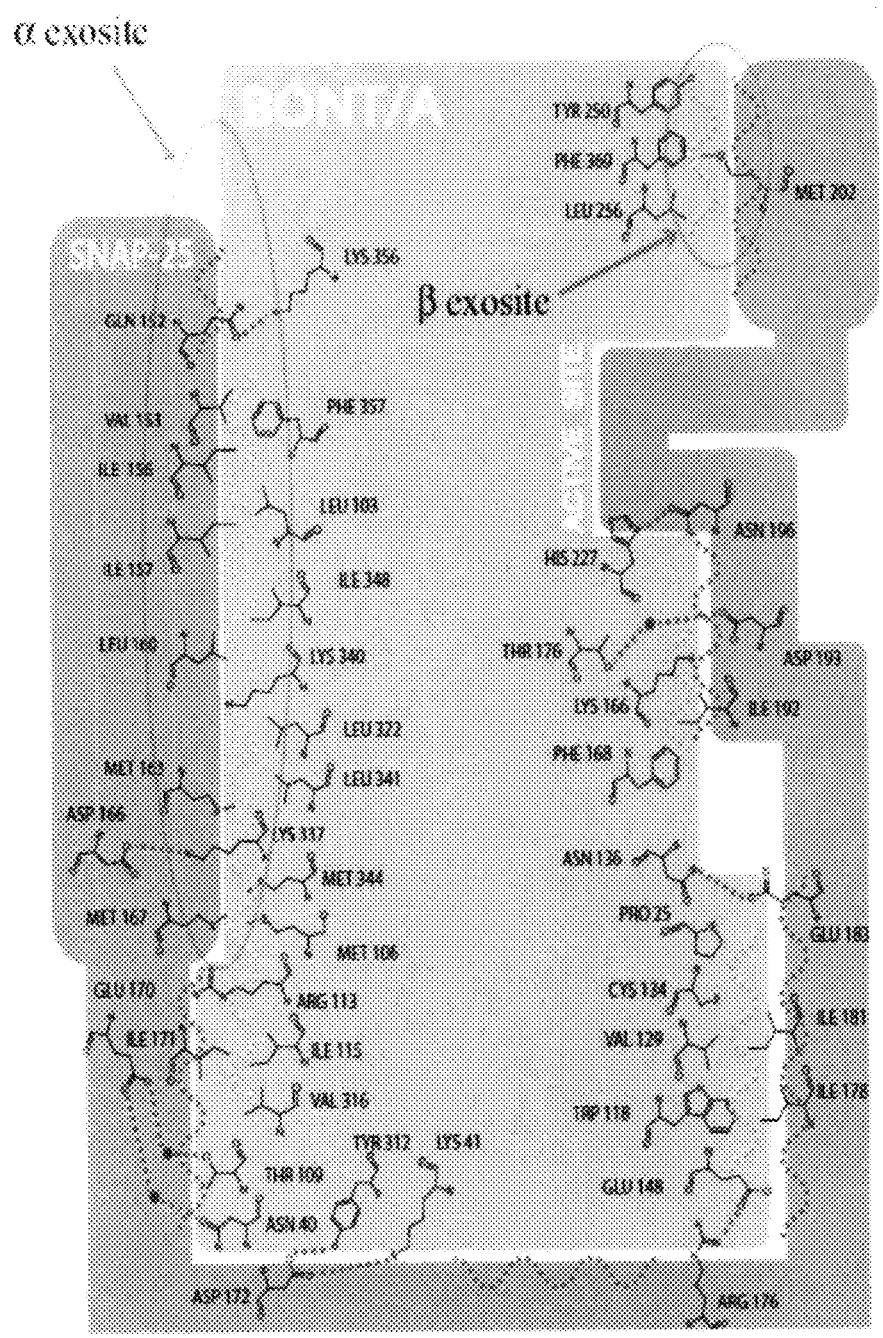
Figure 5 – PRIOR ART

Plasmid Map of pSNAP-tag(T7)-2

Figure 14 (continued)
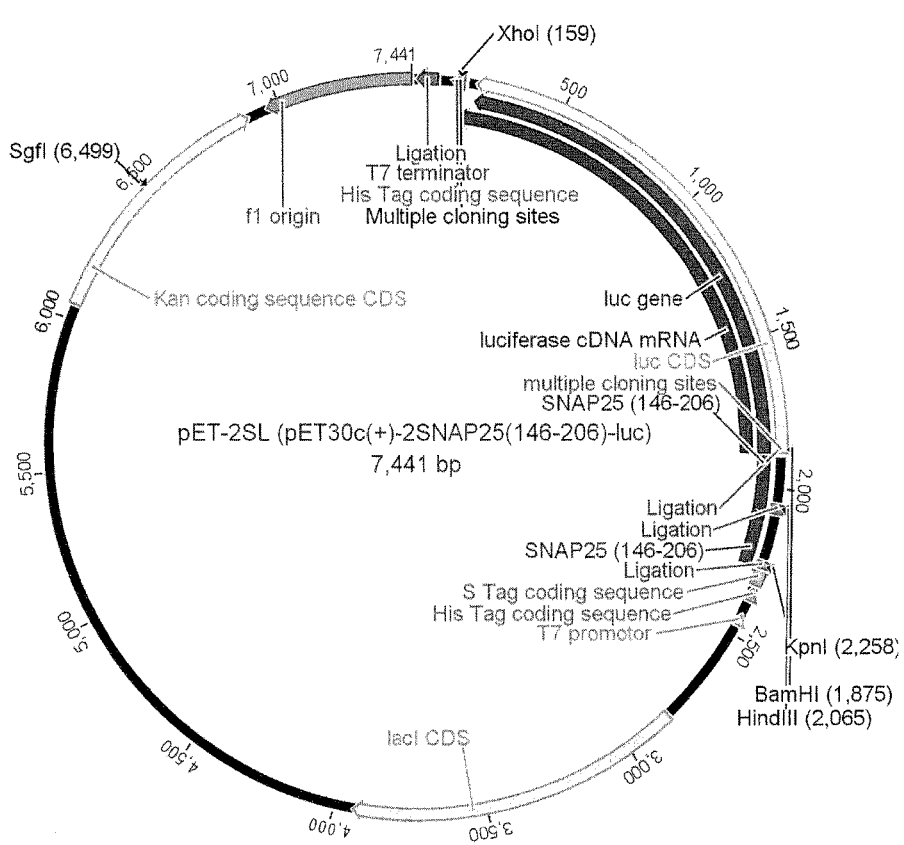
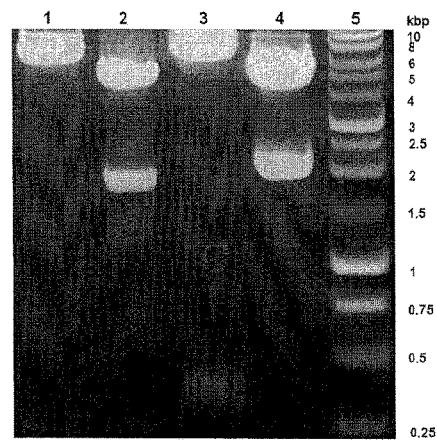

Figure 16
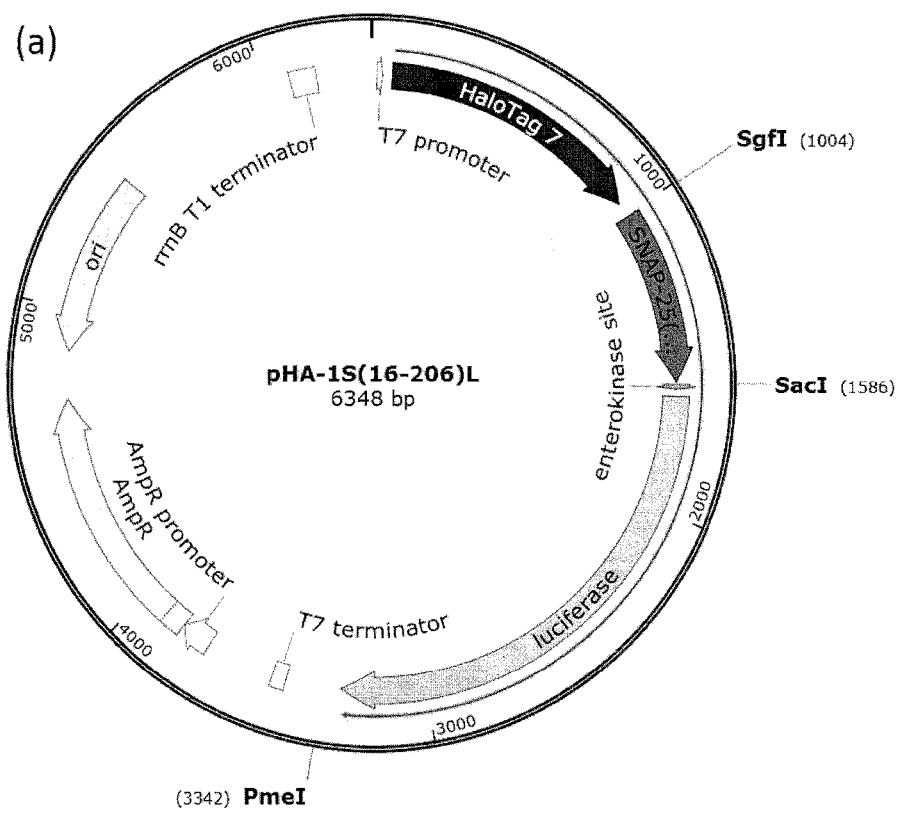
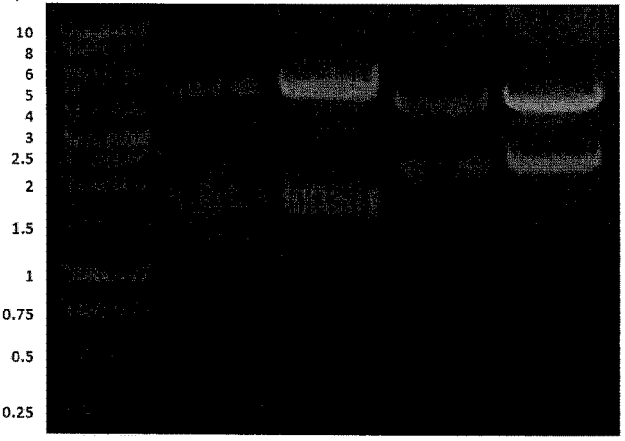

Figure 16 (continued)
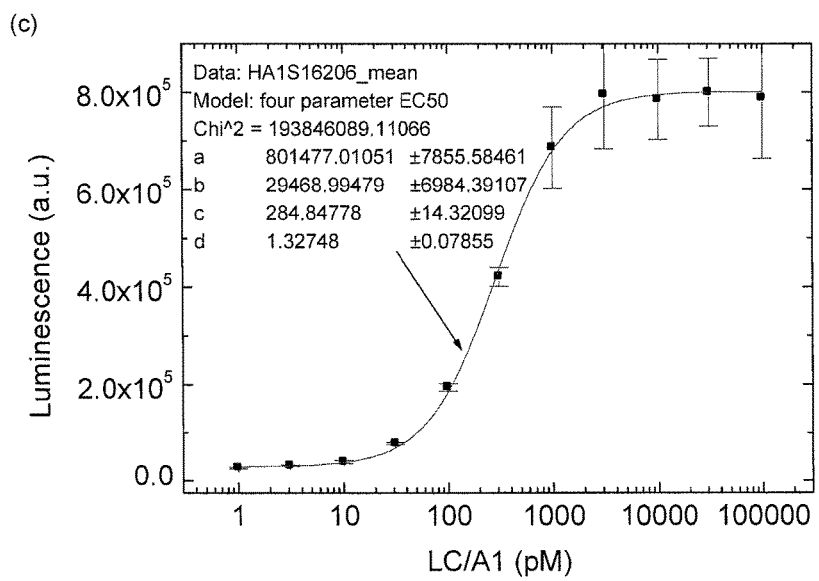
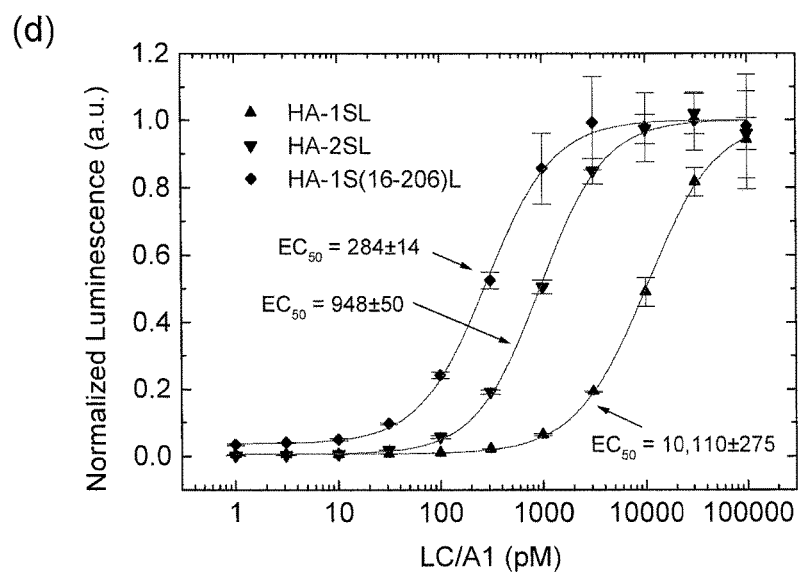

Figure 17
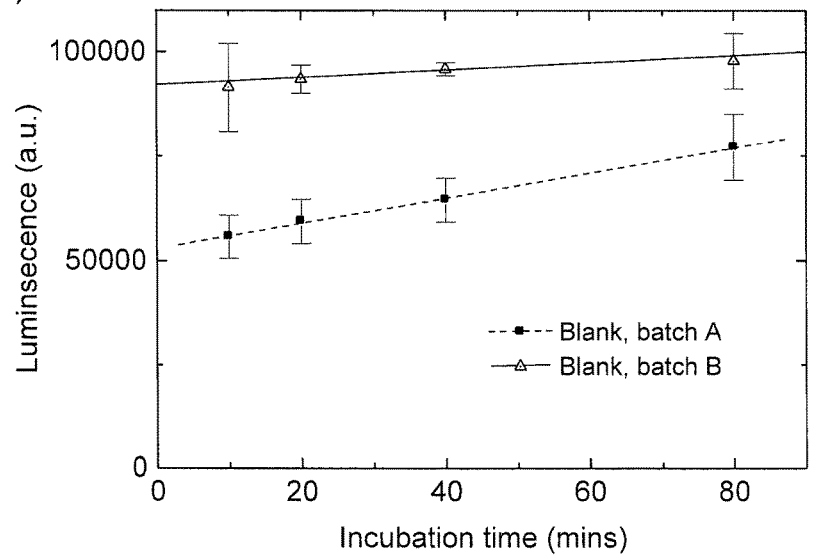
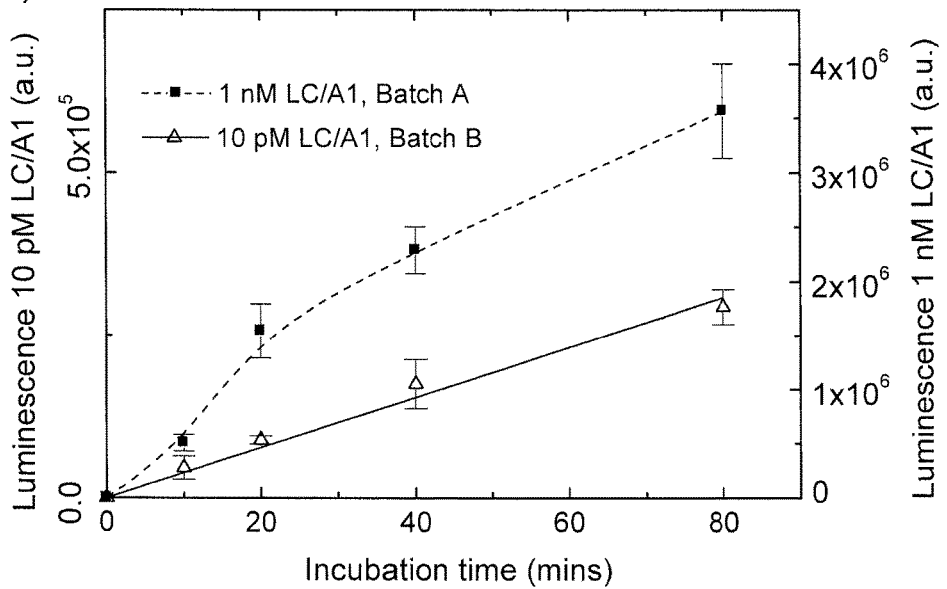

Figure 18
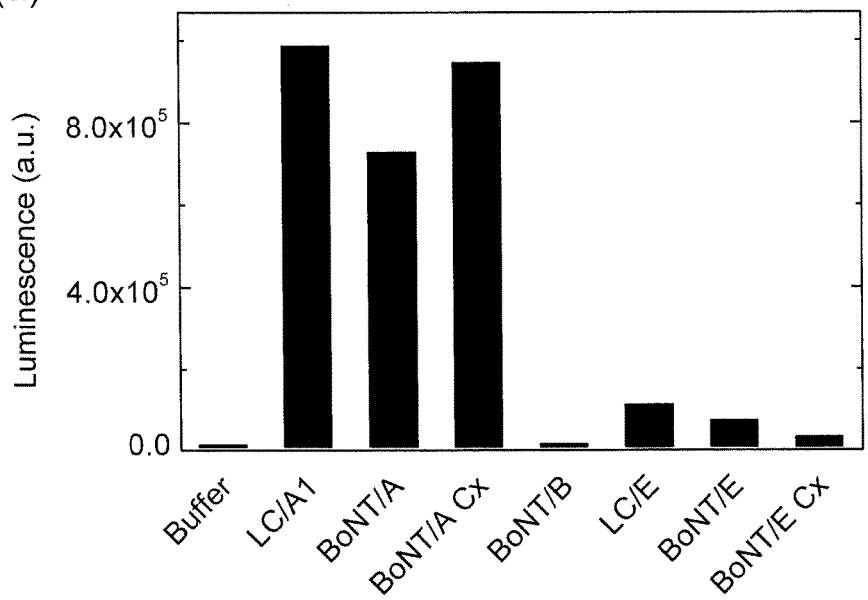
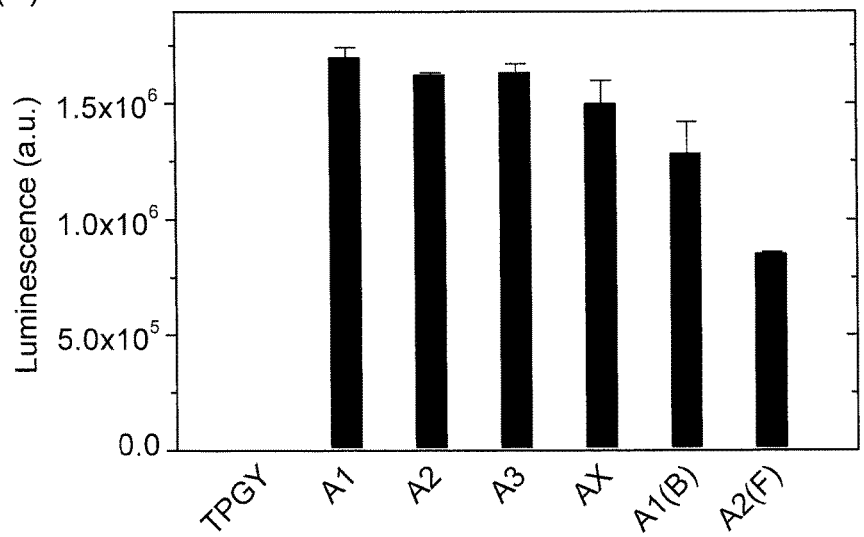

[Bar chart: Luminescence (a.u.) vs Dysport (Mouse LD50 units), Incubation time (mins). Two conditions: "5, 20" and "2, 60". Black bars labeled "Blank", gray bars labeled "Dysport". Values 14.95 above first pair and 7.76 above second pair.]

[Plasmid map: pHA-3SL, 6358 bp. Features labeled: HaloTag 7, SNAP25(146-206), SNAP25, luciferase, T7 terminator, AmpR, AmpR promoter, ori, rrnB T1 terminator. Restriction sites: XhoI (946), SgfI (1004), KpnI (1118), SacII (1309), HindIII (1501), BamHI (1691), PmeI (3352), KpnI (3373), BamHI (3378).]

SEQUENCE LISTING

```
<160> NUMBER OF SEQ ID NOS: 28

<210> SEQ ID NO 1
<211> LENGTH: 206
<212> TYPE: PRT
<213> ORGANISM: Homo sapiens
<220> FEATURE:
<221> NAME/KEY: misc_feature
<223> OTHER INFORMATION: human SNAP25a (Fig. 4c)

<400> SEQUENCE: 1

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205

<210> SEQ ID NO 2
<211> LENGTH: 28
<212> TYPE: DNA
<213> ORGANISM: Artificial sequence
<220> FEATURE:
<223> OTHER INFORMATION: primer

<400> SEQUENCE: 2
gactggtacc atggatgaaa acctagag                                    28

<210> SEQ ID NO 3
<211> LENGTH: 28
<212> TYPE: DNA
<213> ORGANISM: Artificial Sequence
<220> FEATURE:
```

<223> OTHER INFORMATION: primer

<400> SEQUENCE: 3
agtcggatcc caccacttcc cagcatct                                              28

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
gactggtacc atggatgaaa acctagag                                              28

<210> SEQ ID NO 5
<211> LENGTH: 28
<212> TYPE: DNA
<213> ORGANISM: Artificial Sequence
<220> FEATURE:
<223> OTHER INFORMATION: primer

<400> SEQUENCE: 5
ccccaagctt accacttccc agcatctt                                              28

<210> SEQ ID NO 6
<211> LENGTH: 28
<212> TYPE: DNA
<213> ORGANISM: Artificial Sequence
<220> FEATURE:
<223> OTHER INFORMATION: primer

<400> SEQUENCE: 6
gcccaagctt atggatgaaa acctagag                                              28

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
agtcggatcc caccacttcc cagcatct                                              28

<210> SEQ ID NO 8
<211> LENGTH: 55
<212> TYPE: DNA
<213> ORGANISM: Artificial Sequence
<220> FEATURE:
<223> OTHER INFORMATION: primer

<400> SEQUENCE: 8
agtggcgatc gccaaattcg aacgccagca catggacagc ccagatctgg gtacc                55

<210> SEQ ID NO 9
<211> LENGTH: 55
<212> TYPE: DNA
<213> ORGANISM: Artificial Sequence
<220> FEATURE:
<223> OTHER INFORMATION: primer

<400> SEQUENCE: 9
tacggtttaa accaatttgg actttccgcc cttcttggcc tttatgagga tctct               55

-continued

```
<210> SEQ ID NO 10
<211> LENGTH: 55
<212> TYPE: DNA
<213> ORGANISM: Artificial Sequence
<220> FEATURE:
<223> OTHER INFORMATION: primer

<400> SEQUENCE: 10
agtggcgatc gctaaattcg aacgccagca catggacagc ccagatctgg gtacc      55

<210> SEQ ID NO 11
<211> LENGTH: 55
<212> TYPE: DNA
<213> ORGANISM: Artificial Sequence
<220> FEATURE:
<223> OTHER INFORMATION: primer

<400> SEQUENCE: 11
tacggtttaa accaatttgg actttccgcc cttcttggcc tttatgagga tctct      55

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12
gactggtacc atggatgaaa acctagag                                    28

<210> SEQ ID NO 13
<211> LENGTH: 28
<212> TYPE: DNA
<213> ORGANISM: Artificial Sequence
<220> FEATURE:
<223> OTHER INFORMATION: Primer

<400> SEQUENCE: 13
agtcggatcc caccacttcc cagcatct                                    28

<210> SEQ ID NO 14
<211> LENGTH: 28
<212> TYPE: DNA
<213> ORGANISM: Artificial Sequence
<220> FEATURE:
<223> OTHER INFORMATION: Primer

<400> SEQUENCE: 14
gactggtacc atggatgaaa acctagag                                    28

<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15
ccccaagctt accacttccc agcatctt                                    28

<210> SEQ ID NO 16
<211> LENGTH: 28
<212> TYPE: DNA
<213> ORGANISM: Artificial Sequence
<220> FEATURE:
<223> OTHER INFORMATION: Primer
```

```
<400> SEQUENCE: 16
gcccaagctt atggatgaaa acctagag                                           28

<210> SEQ ID NO 17
<211> LENGTH: 28
<212> TYPE: DNA
<213> ORGANISM: Artificial Sequence
<220> FEATURE:
<223> OTHER INFORMATION: Primer

<400> SEQUENCE: 17
agtcggatcc caccacttcc cagcatct                                           28

<210> SEQ ID NO 18
<211> LENGTH: 33
<212> TYPE: DNA
<213> ORGANISM: Artificial Sequence
<220> FEATURE:
<223> OTHER INFORMATION: Primer

<400> SEQUENCE: 18
actggcgatc gcgcgaaggg ctgaccagtt ggc                                     33

<210> SEQ ID NO 19
<211> LENGTH: 34
<212> TYPE: DNA
<213> ORGANISM: Artificial Sequence
<220> FEATURE:
<223> OTHER INFORMATION: Primer

<400> SEQUENCE: 19
tgacgagctc accacttccc agcatctttg ttgc                                    34

<210> SEQ ID NO 20
<211> LENGTH: 32
<212> TYPE: DNA
<213> ORGANISM: Artificial Sequence
<220> FEATURE:
<223> OTHER INFORMATION: Primer

<400> SEQUENCE: 20
gatcgctagc gccgacgacg acgacaaggc ca                                      32

<210> SEQ ID NO 21
<211> LENGTH: 38
<212> TYPE: DNA
<213> ORGANISM: Artificial Sequence
<220> FEATURE:
<223> OTHER INFORMATION: Primer

<400> SEQUENCE: 21
tagggtttaa acggcctcgg aggattacaa tagctaag                                38

<210> SEQ ID NO 22
<211> LENGTH: 61
<212> TYPE: PRT
<213> ORGANISM: Homo sapiens

<400> SEQUENCE: 22

Met Asp Glu Asn Leu Glu Gln Val Ser Gly Ile Ile Gly Asn Leu Arg
1               5                   10                  15

His Met Ala Leu Asp Met Gly Asn Glu Ile Asp Thr Gln Asn Arg Gln
            20                  25                  30

Ile Asp Arg Ile Met Glu Lys Ala Asp Ser Asn Lys Thr Arg Ile Asp
```

Glu Ala Asn Gln Arg Ala Thr Lys Met Leu Gly Ser Gly
    50              55                  60

<210> SEQ ID NO 23
<211> LENGTH: 61
<212> TYPE: PRT
<213> ORGANISM: Artificial Sequence
<220> FEATURE:
<223> OTHER INFORMATION: amino acids 146-206 of human SNAP25 with I181E
      mutation

<400> SEQUENCE: 23

Met Asp Glu Asn Leu Glu Gln Val Ser Gly Ile Ile Gly Asn Leu Arg
1               5                   10                  15

His Met Ala Leu Asp Met Gly Asn Glu Ile Asp Thr Gln Asn Arg Gln
            20                  25                  30

Ile Asp Arg Glu Met Glu Lys Ala Asp Ser Asn Lys Thr Arg Ile Asp
        35                  40                  45

Glu Ala Asn Gln Arg Ala Thr Lys Met Leu Gly Ser Gly
    50              55                  60

<210> SEQ ID NO 24
<211> LENGTH: 61
<212> TYPE: PRT
<213> ORGANISM: Artificial Sequence
<220> FEATURE:
<223> OTHER INFORMATION: amino acids 146-206 of human SNAP25 with R198E
      mutation

<400> SEQUENCE: 24

Met Asp Glu Asn Leu Glu Gln Val Ser Gly Ile Ile Gly Asn Leu Arg
1               5                   10                  15

His Met Ala Leu Asp Met Gly Asn Glu Ile Asp Thr Gln Asn Arg Gln
            20                  25                  30

Ile Asp Arg Ile Met Glu Lys Ala Asp Ser Asn Lys Thr Arg Ile Asp
        35                  40                  45

Glu Ala Asn Gln Glu Ala Thr Lys Met Leu Gly Ser Gly
    50              55                  60

<210> SEQ ID NO 25
<211> LENGTH: 191
<212> TYPE: PRT
<213> ORGANISM: Homo sapiens

<400> SEQUENCE: 25

Arg Arg Ala Asp Gln Leu Ala Asp Glu Ser Leu Glu Ser Thr Arg Arg
1               5                   10                  15

Met Leu Gln Leu Val Glu Glu Ser Lys Asp Ala Gly Ile Arg Thr Leu
            20                  25                  30

Val Met Leu Asp Glu Gln Gly Glu Gln Leu Asp Arg Val Glu Glu Gly
        35                  40                  45

Met Asn His Ile Asn Gln Asp Met Lys Glu Ala Glu Lys Asn Leu Lys
    50              55                  60

Asp Leu Gly Lys Cys Cys Gly Leu Phe Ile Cys Pro Cys Asn Lys Leu
65                  70                  75                  80

Lys Ser Ser Asp Ala Tyr Lys Lys Ala Trp Gly Asn Asn Gln Asp Gly
                85                  90                  95

Val Val Ala Ser Gln Pro Ala Arg Val Val Asp Glu Arg Glu Gln Met
            100                 105                 110

```
Ala Ile Ser Gly Gly Phe Ile Arg Arg Val Thr Asn Asp Ala Arg Glu
        115                 120                 125

Asn Glu Met Asp Glu Asn Leu Glu Gln Val Ser Gly Ile Ile Gly Asn
    130                 135                 140

Leu Arg His Met Ala Leu Asp Met Gly Asn Glu Ile Asp Thr Gln Asn
145                 150                 155                 160

Arg Gln Ile Asp Arg Ile Met Glu Lys Ala Asp Ser Asn Lys Thr Arg
                165                 170                 175

Ile Asp Glu Ala Asn Gln Arg Ala Thr Lys Met Leu Gly Ser Gly
            180                 185                 190
```

<210> SEQ ID NO 26
<211> LENGTH: 191
<212> TYPE: PRT
<213> ORGANISM: Artificial Sequence
<220> FEATURE:
<223> OTHER INFORMATION: Human SNAP-25 amino acids 16-206, with point
      mutations C84S, C85S, C90S and C92S

<400> SEQUENCE: 26

```
Arg Arg Ala Asp Gln Leu Ala Asp Glu Ser Leu Glu Ser Thr Arg Arg
1               5                   10                  15

Met Leu Gln Leu Val Glu Glu Ser Lys Asp Ala Gly Ile Arg Thr Leu
            20                  25                  30

Val Met Leu Asp Glu Gln Gly Glu Gln Leu Asp Arg Val Glu Glu Gly
        35                  40                  45

Met Asn His Ile Asn Gln Asp Met Lys Glu Ala Glu Lys Asn Leu Lys
50                  55                  60

Asp Leu Gly Lys Ser Ser Gly Leu Phe Ile Ser Pro Ser Asn Lys Leu
65                  70                  75                  80

Lys Ser Ser Asp Ala Tyr Lys Lys Ala Trp Gly Asn Asn Gln Asp Gly
                85                  90                  95

Val Val Ala Ser Gln Pro Ala Arg Val Val Asp Glu Arg Glu Gln Met
            100                 105                 110

Ala Ile Ser Gly Gly Phe Ile Arg Arg Val Thr Asn Asp Ala Arg Glu
        115                 120                 125

Asn Glu Met Asp Glu Asn Leu Glu Gln Val Ser Gly Ile Ile Gly Asn
    130                 135                 140

Leu Arg His Met Ala Leu Asp Met Gly Asn Glu Ile Asp Thr Gln Asn
145                 150                 155                 160

Arg Gln Ile Asp Arg Ile Met Glu Lys Ala Asp Ser Asn Lys Thr Arg
                165                 170                 175

Ile Asp Glu Ala Asn Gln Arg Ala Thr Lys Met Leu Gly Ser Gly
            180                 185                 190
```

<210> SEQ ID NO 27
<211> LENGTH: 116
<212> TYPE: PRT
<213> ORGANISM: Homo sapiens

<400> SEQUENCE: 27

```
Met Ser Ala Thr Ala Ala Thr Ala Pro Pro Ala Ala Pro Ala Gly Glu
1               5                   10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45
```

-continued

```
Asn Val Asp Lys Val Leu Glu Arg Asp Gln Lys Leu Ser Glu Leu Asp
     50                  55                  60

Asp Arg Ala Asp Ala Leu Gln Ala Gly Ala Ser Gln Phe Glu Thr Ser
 65              70                  75                  80

Ala Ala Lys Leu Lys Arg Lys Tyr Trp Trp Lys Asn Leu Lys Met Met
             85                  90                  95

Ile Ile Leu Gly Val Ile Cys Ala Ile Ile Leu Ile Ile Ile Ile Val
            100                 105                 110

Tyr Phe Ser Thr
            115

<210> SEQ ID NO 28
<211> LENGTH: 97
<212> TYPE: PRT
<213> ORGANISM: Homo sapiens

<400> SEQUENCE: 28

Met Ser Ala Thr Ala Ala Thr Ala Pro Pro Ala Ala Pro Ala Gly Glu
 1               5                  10                  15

Gly Gly Pro Pro Ala Pro Pro Pro Asn Leu Thr Ser Asn Arg Arg Leu
             20                  25                  30

Gln Gln Thr Gln Ala Gln Val Asp Glu Val Val Asp Ile Met Arg Val
             35                  40                  45

Asn Val Asp Lys Val Leu Glu Arg Asp Gln Lys Leu Ser Glu Leu Asp
     50                  55                  60

Asp Arg Ala Asp Ala Leu Gln Ala Gly Ala Ser Gln Phe Glu Thr Ser
 65              70                  75                  80

Ala Ala Lys Leu Lys Arg Lys Tyr Trp Trp Lys Asn Leu Lys Met Met
             85                  90                  95

Ile
```

ASSAY FOR CLOSTRIDIUM BOTULINUM NEUROTOXIN

SEQUENCE LISTING

The instant application contains a Sequence Listing that has been submitted in ASCII format via EFS-Web and is hereby incorporated by reference in its entirety. Said ASCII copy, created on Apr. 3, 2014, is named LNK_151US_SequenceListing.txt and is 13,064 bytes in size.

PRIORITY

This application corresponds to the national phase of International Application No. PCT/EP2012067100, filed Sep. 3, 2012, which, in turn, claims priority to European Patent Application No. 11.184030.2 filed Oct. 5, 2011, both of which are incorporated by reference herein in their entirety.

FIELD OF THE INVENTION

The present invention relates to a method of determining Botulinum toxin (BoNT) based on a luminescence assay. The present application further relates to a peptide that is susceptible to proteolytic cleavage by BoNT which is suitable for that method.

BACKGROUND OF THE INVENTION

Botulinum NeuroToxin (BoNT) is a 150 kDa protein produced by anaerobic bacteria species, most notably *Clostridium botulinum*, that causes life-threatening botulism. BoNT causes disease by preventing the release of neurotransmitters at distinct synapses (Humeau, Doussau et al. 2000), blocking nerve impulses and resulting in a flaccid paralysis. Release of neurotransmitters is blocked by proteolytic activity of a 50 kDa fragment of BoNT called the light chain (LC). This is a $Zn^{2+}$ containing endoprotease.

There are seven known serotypes of BoNT, labelled A to G, which are distinguished from each other by antibody neutralization assays. Type A is commonly associated with botulism in humans. Crystalline BoNT-A (Mw=900,000) consists of two BoNT Type A molecules (Mw=150,000) and a number of non-toxic Neurotoxin Associated Proteins (NAP) that help shield the toxin against acidic and proteolytic attack in the gastro intestinal tract.

Detection of BoNT at relevant concentrations is challenging because it is highly lethal and therefore a test for it must be correspondingly sensitive. Lethal amounts of crystalline BoNT type A per kg body weight in humans is estimated from primate studies to be 1 μg when taken orally, 1.3-2.2 ng intravenously or intramuscularly, and 10-12.9 ng by inhalation. Assuming 70 kg body weight and 5 liters of peripheral blood for an average adult, this would correspond to a lethal concentration of 18.2-30.8 ng/L crystalline BoNT/A (0.040-0.069 pM BoNT/A).

The currently accepted test for BoNT is the standard mouse bioassay. This requires intraperitoneal injection of two or more 20-30 g mice with 0.4-0.5 ml of filter sterilized sample, and watching for signs of intoxication. BoNT intoxicated mice will usually die within 6-96 hours, depending on the level of toxin in the sample. The LD50 of crystalline BoNT Type A for mice is 0.03 ng which corresponds to 5 pg of pure BoNT-A (Schantz and Johnson 1992).

The mouse bioassay causes severe distress, cannot be used in the field, is time consuming, cost intensive and it is impractical for screening large numbers of samples. In response to the need for a rapid and sensitive assay for BoNT, in vitro assays have been under development in recent years.

Assays that detect BoNT proteolytic activity employ naturally occurring or synthetic substrates of LC, together with methods for detecting the cleaved products. These include antibodies against the cleaved fragments, mass spectrometry, and fluorescence.

The first fluorescence-reporter assays employed fluorescein markers immobilized by cleavable peptides that were released by BoNT proteolytic activity, or Förster Resonance Energy Transfer (FRET) between a chromophore quencher and a fluorophore. FRET was inactivated by BoNT proteolytic activity and this was detected by changes in fluorescence. Other fluorescence-based assays for proteolytic activity were subsequently developed using similar principles of operation: either detection of released fluorophores, or fluorescence signals associated with FRET.

WO 2004/031355 A2 describes an assay for the detection of botulinum toxin based on proteolytic cleavage of SNAP25. The construct used comprises a hexahistidine tag and a fluorescent molecule for detection. The sensitivity of the assay (FIG. 3B) is said to be down to 1.0 ng/ml BoNT/A holotoxin (6.6 pM). A higher sensitivity of an assay for the detection of botulinum toxin is desirable (<0.1 pM).

SUMMARY OF THE INVENTION

It is one object of the present invention to provide a sensitive assay for the detection of BoNT.

The inventors of this application surprisingly found that the sensitivity of an assay for the detection of BoNT based on proteolytic cleavage of SNAP25 can be increased if a bioluminescent marker is used instead of a fluorescent marker:

The inventors further found that, unexpectedly, the sensitivity of such an assay can be increased if the peptide to be cleaved is covalently attached to a support.

The present invention therefore relates to a method of determining Botulinum toxin (BoNT) comprising the steps of
a) providing a peptide comprising
   an amino acid sequence susceptible to proteolytic cleavage by BoNT,
   the amino acid sequence of luciferase, preferably firefly luciferase, preferably in series to the amino acid sequence susceptible to proteolytic cleavage by BoNT, and
   a tag suitable for attaching the peptide to a support,
b) attaching said peptide to a support,
c) adding the test sample to be investigated for presence or amount of BoNT, and
d) determining the luminescence signal of the released luciferase.

In another embodiment, the invention relates to a method of determining Botulinum toxin (BoNT) comprising the steps of
a) providing a peptide comprising
   an amino acid sequence susceptible to proteolytic cleavage by BoNT,
   the amino acid sequence of a reporter domain, preferably in series to the amino acid sequence susceptible to proteolytic cleavage by BoNT, and
   a tag suitable for attaching the peptide to a support, b) covalently attaching said peptide to the support, c) adding the test sample to be investigated for presence or amount of BoNT, and d) determining the signal released by the reporter domain.

(a) Firefly luciferase tethered to a magnetic bead is cut free by BoNT.

(b) Freed luciferase molecule interacts with multiple substrate molecules to provide an amplified luminescence signal.

Figure 3:
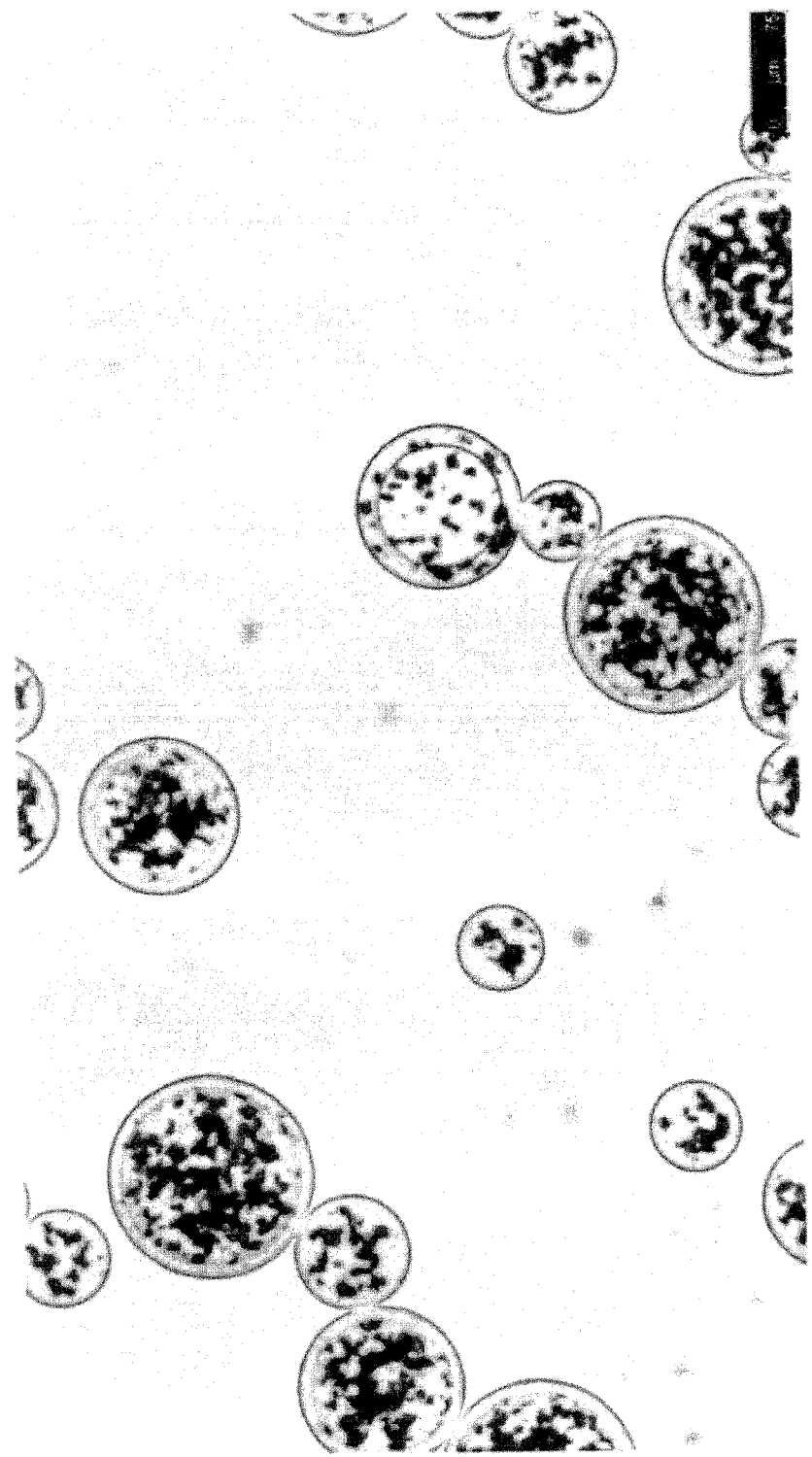

FIG. 3. Microscope image of HaloLink Magnetic Beads, used in this assay for detecting BoNT.

Figure 4A:
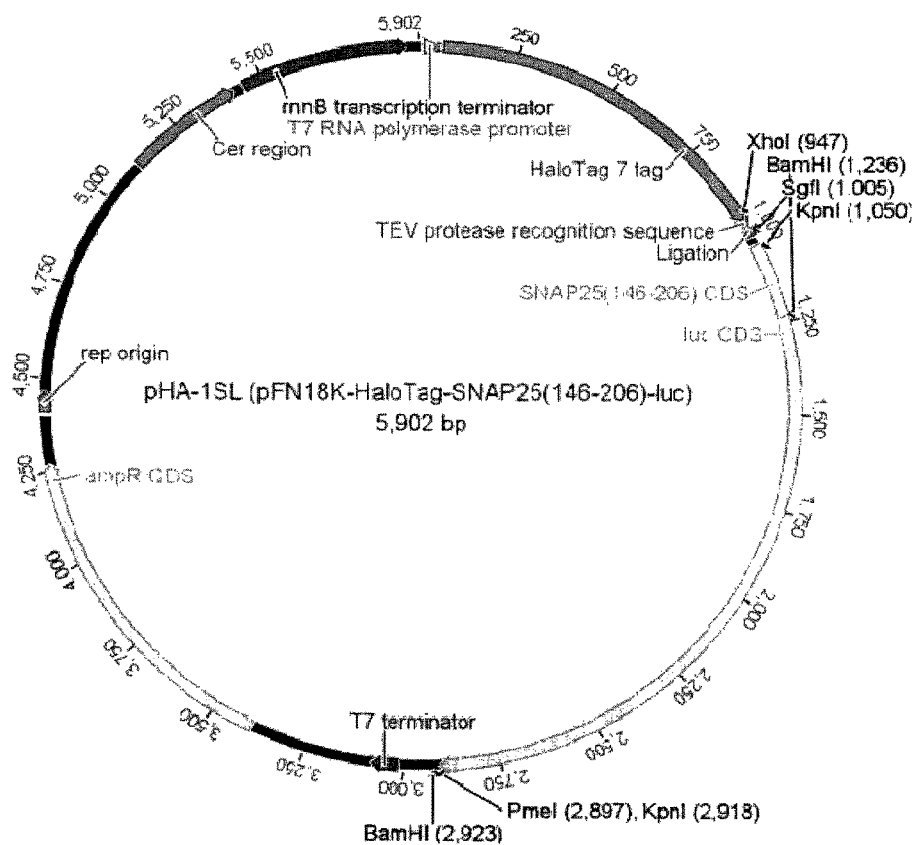

FIG. 4. Restriction maps of (a) pHA-1SL and (b) pHA-2SL, plasmids encoding proteins used in the assay for detecting BoNT types A, C and E. pHA-2SL is identical to pHA-1SL except that there are two SNAP-25 (amino acids 146-206) sequences between the HaloTag and Luciferase protein coding sequence (CDS).

(c) Human SNAP25A amino acid sequence showing the cleavage site (dotted lines) for BoNT types A, C and E. Amino acid residues are coded as follows: acidic, basic, neutral, hydrophobic and unique residues.

FIG. 5. A schematic diagram of the interface between human SNAP-25 amino acids 141-204 (the dark shaded outer ring) and BoNT/A-L (the light shaded inner ring). Both the a and β exosites are indicated. Residues involved in side-chain/side-chain interactions are explicitly shown. Dashed indicate polar side-chain contacts, with water mediation indicated by red dots. An outer set of wavy lines indicates regions of hydrophobic side-chain interaction. An inner set of wavy lines indicates regions of backbone polar contacts (Breidenbach and Brunger 2004).

Figure 6:
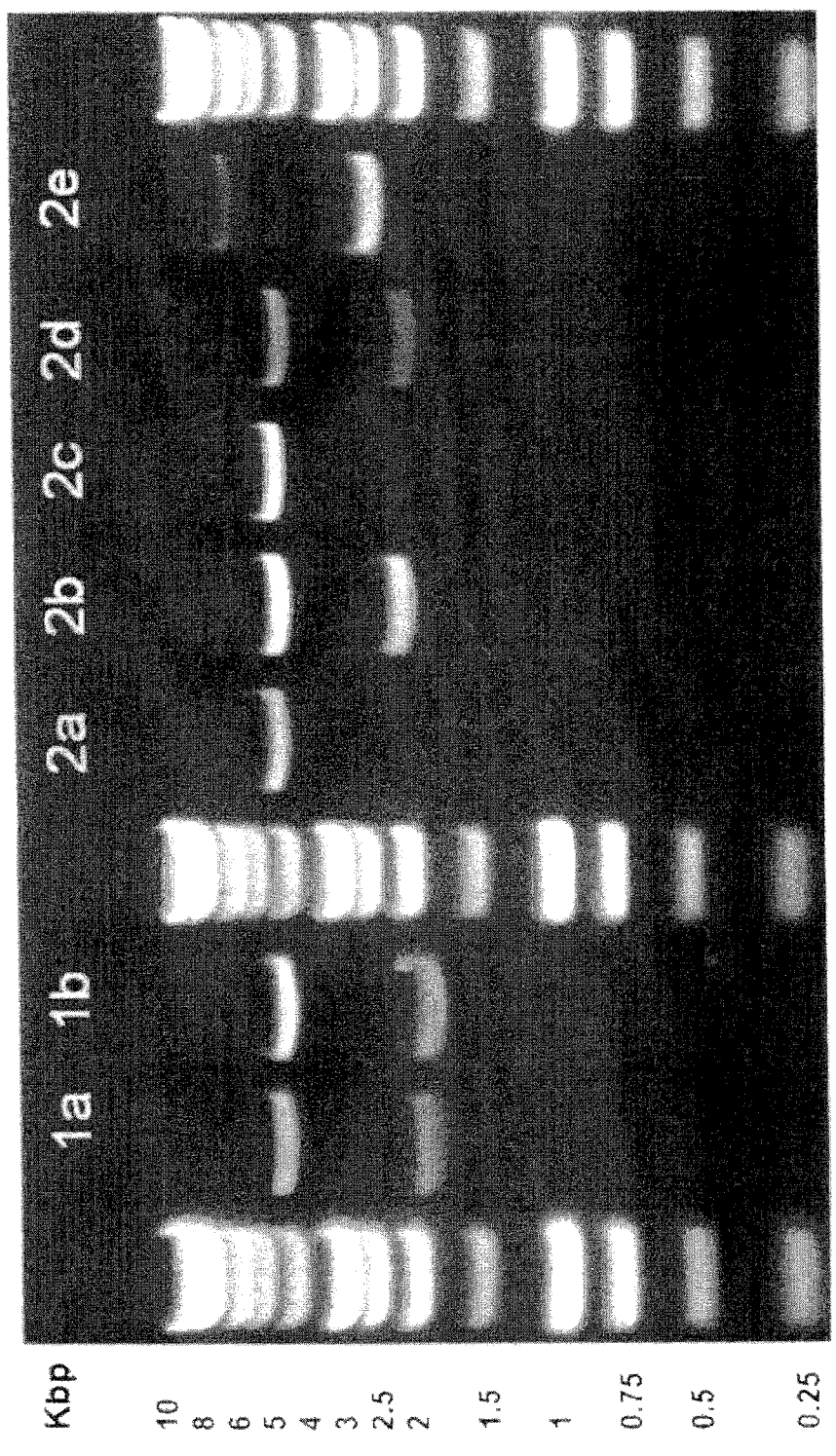

FIG. 6. Gel Electrophoresis of Sgf I/Pme I digestion products of cells thought to be transformed with pHA-1SL (lanes 1a and 1b) and pHA-2SL (lanes 2a-2e): 1% agar stained with Ethidium bromide (Protocol 92).

Figure 7:
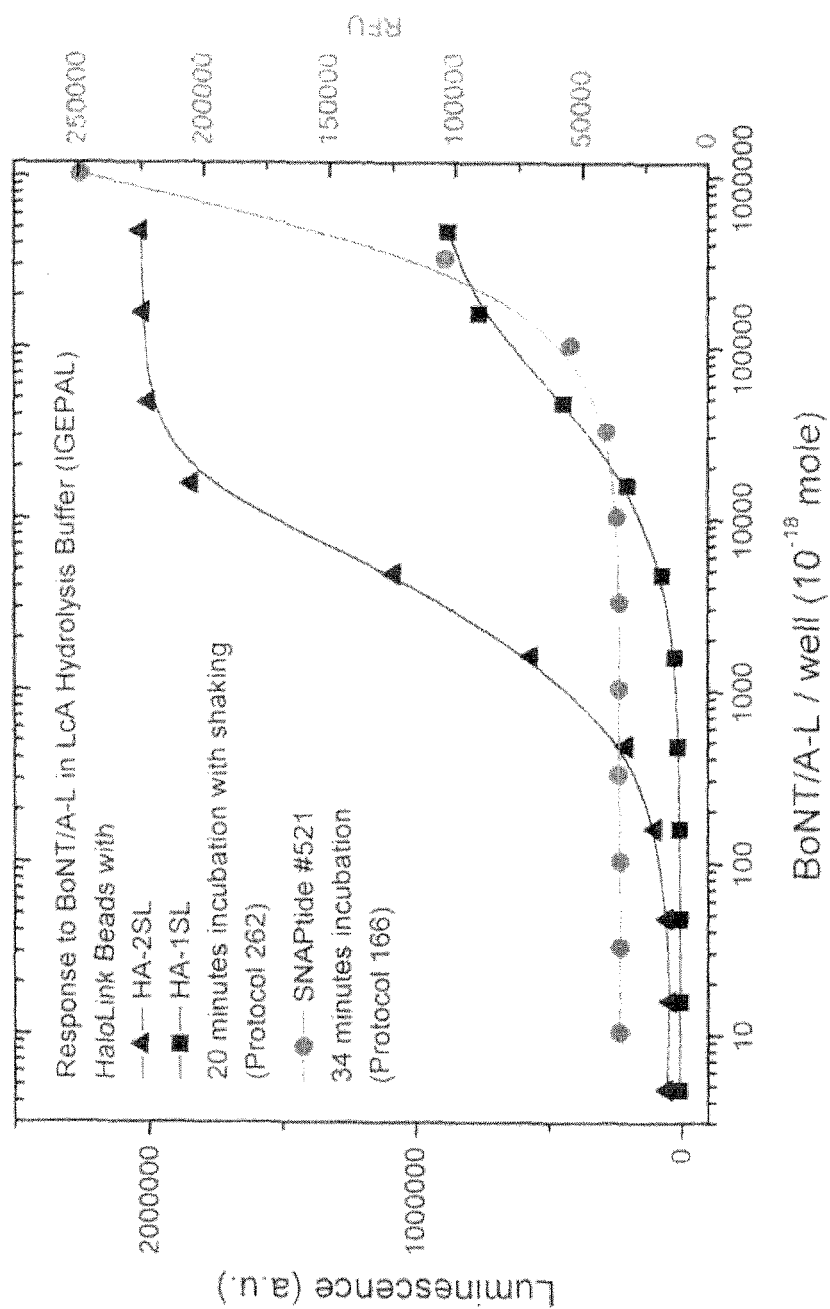

FIG. 7. Response of the assay with one and two SNAP-25 sequences, and SNAPtide #521, to LcA Buffer spiked with recombinant BoNT/A-L.

Figure 8:
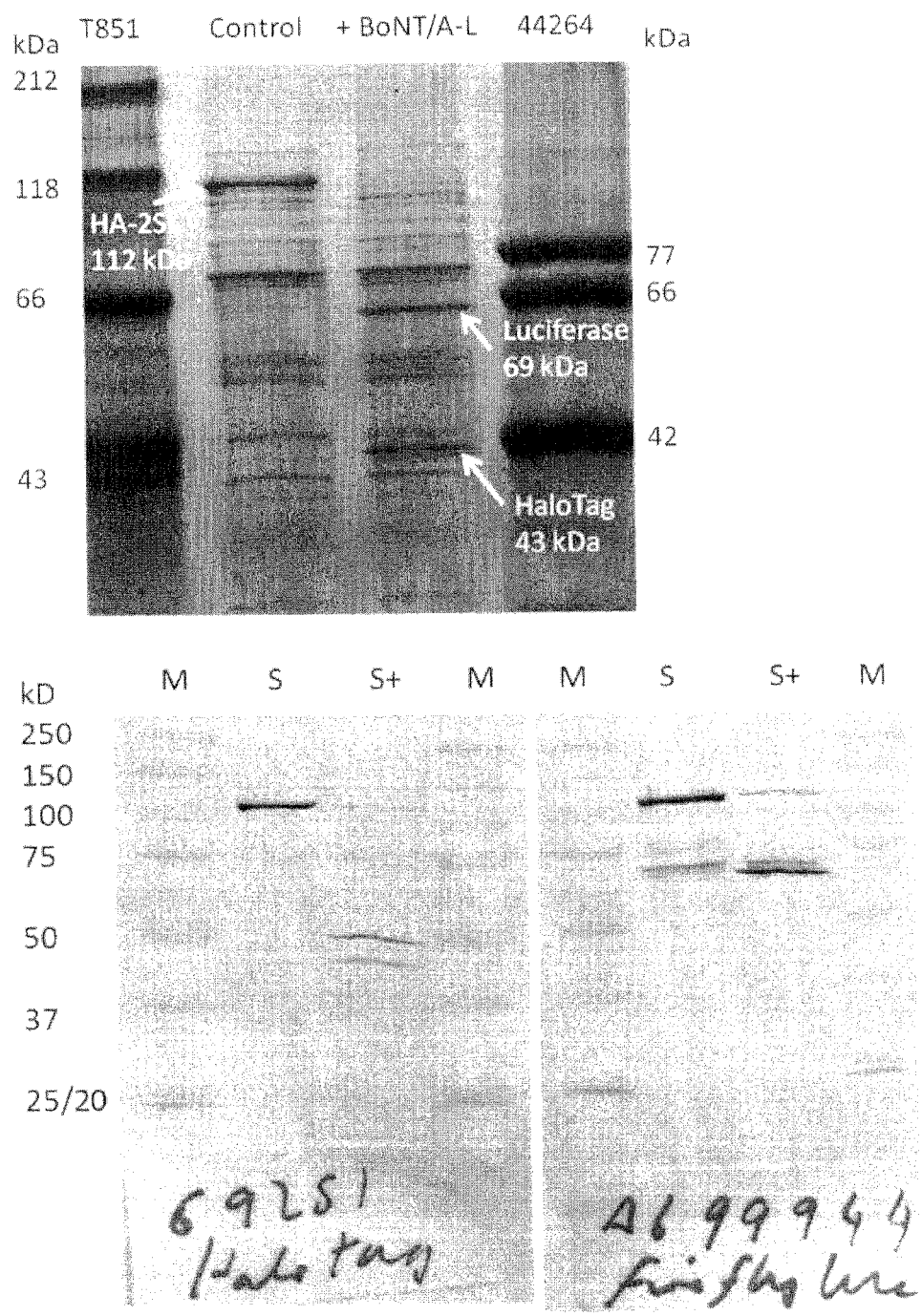

FIG. 8. Top: SDS PAGE of protein HA-2SL from purified cell lysate before (control) and after incubation with recombinant BoNT/A-L. Lanes marked 'T851' and '44264' are protein markers. Bottom: Western Blot of HA-2SL, a protein consisting of HaloTag, two sequences of SNAP25 amino acids 146-206 and luciferase. This protein is in lanes marked S. After incubation of HA-2SL with BoNT/A light chain, the products are in lanes marked S+. The protein marker is in lanes marked M. The membrane on the left was treated with antibody against HaloTag, the membrane on the right was treated with antibody against luciferase.

Figure 9:
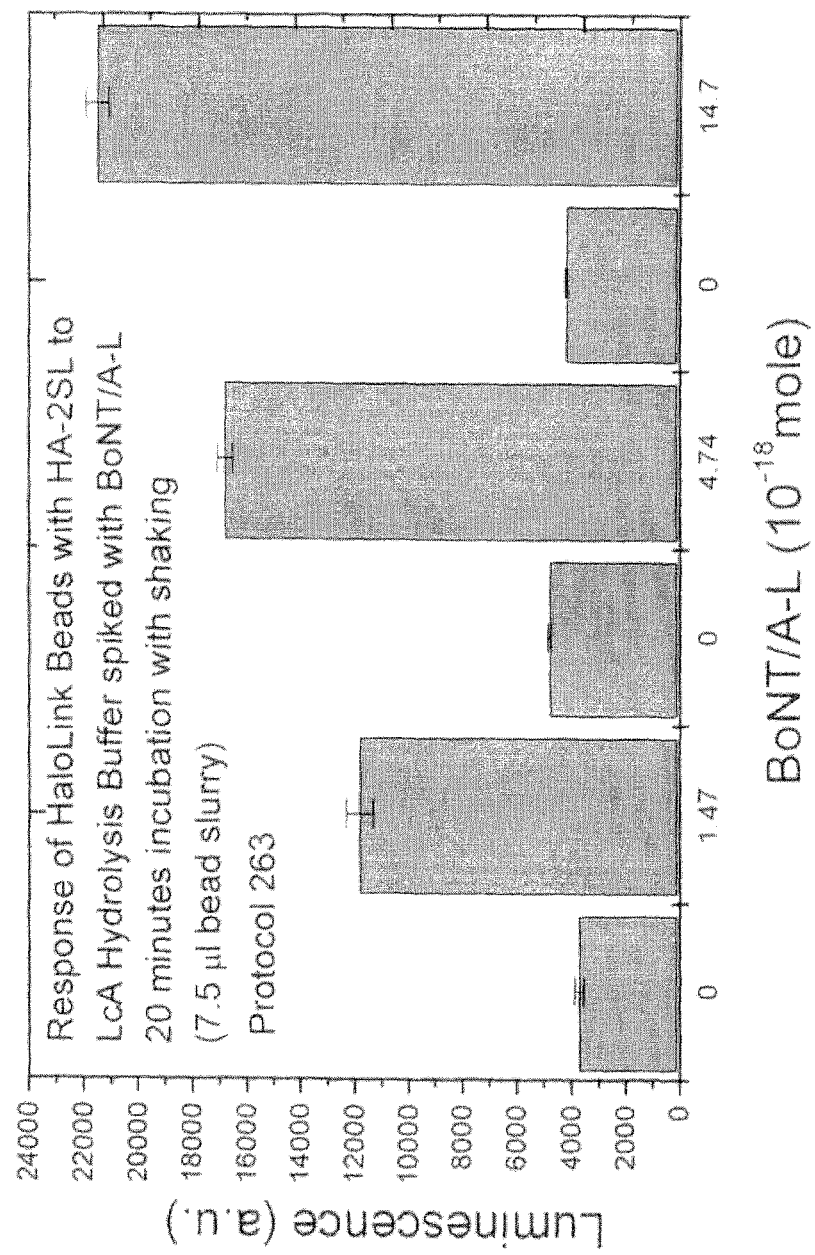

FIG. 9. Response of the assay to various amounts of recombinant BoNT/A-L in LcA Hydrolysis Buffer. Error bars are the SEM of 6 measurements.

Figure 10:
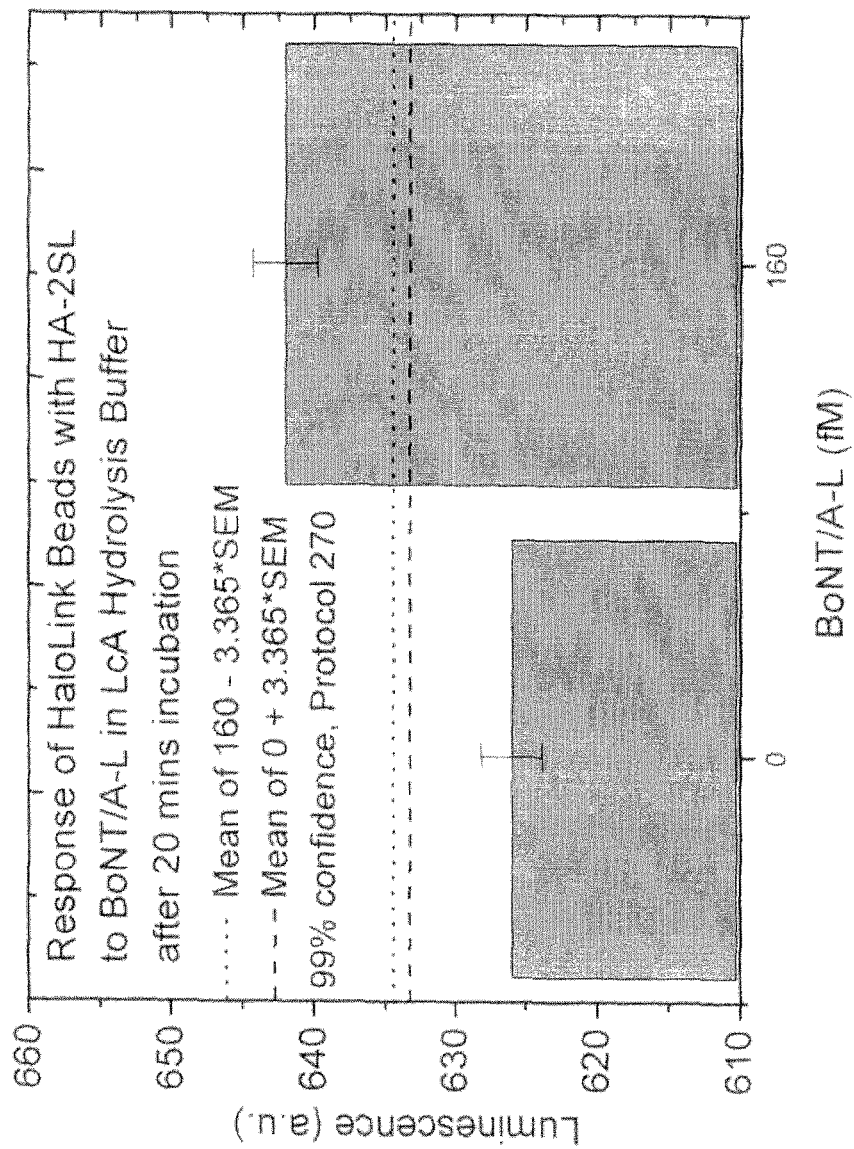

FIG. 10. Mean response of the assay to LcA Hydrolysis Buffer with 80 pM Cetyl Trimethyl Ammonium Bromide (CTAB) spiked with BoNT/A-L, after 20 minutes incubation. Error bars are the SEM of 6 measurements, 99% confidence intervals above and below mean values. Note the scale on the y axis begins at 610.

Figure 11:
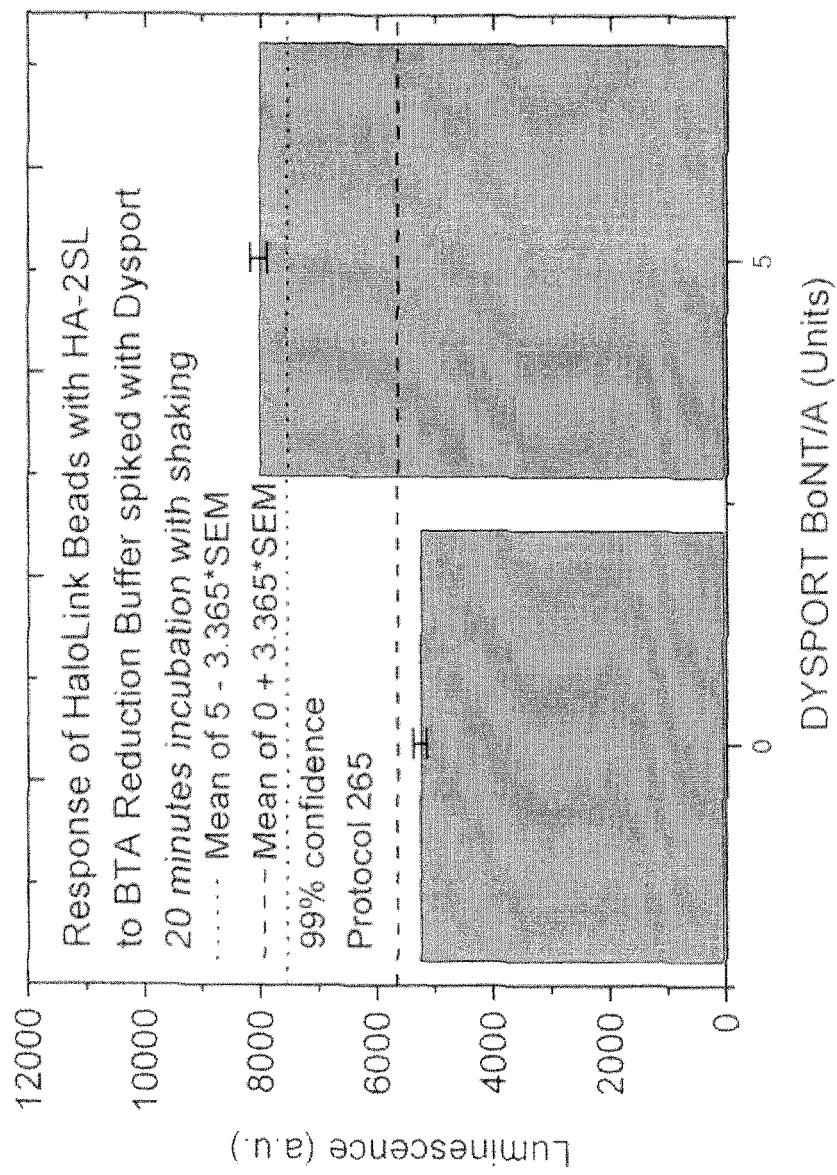

FIG. 11. Mean response of the assay to BTA Reduction Buffer spiked with 5 Units Dysport. Error bars are the SEM of 6 measurements, 99% conficence intervals above and below mean values.

Figure 12:
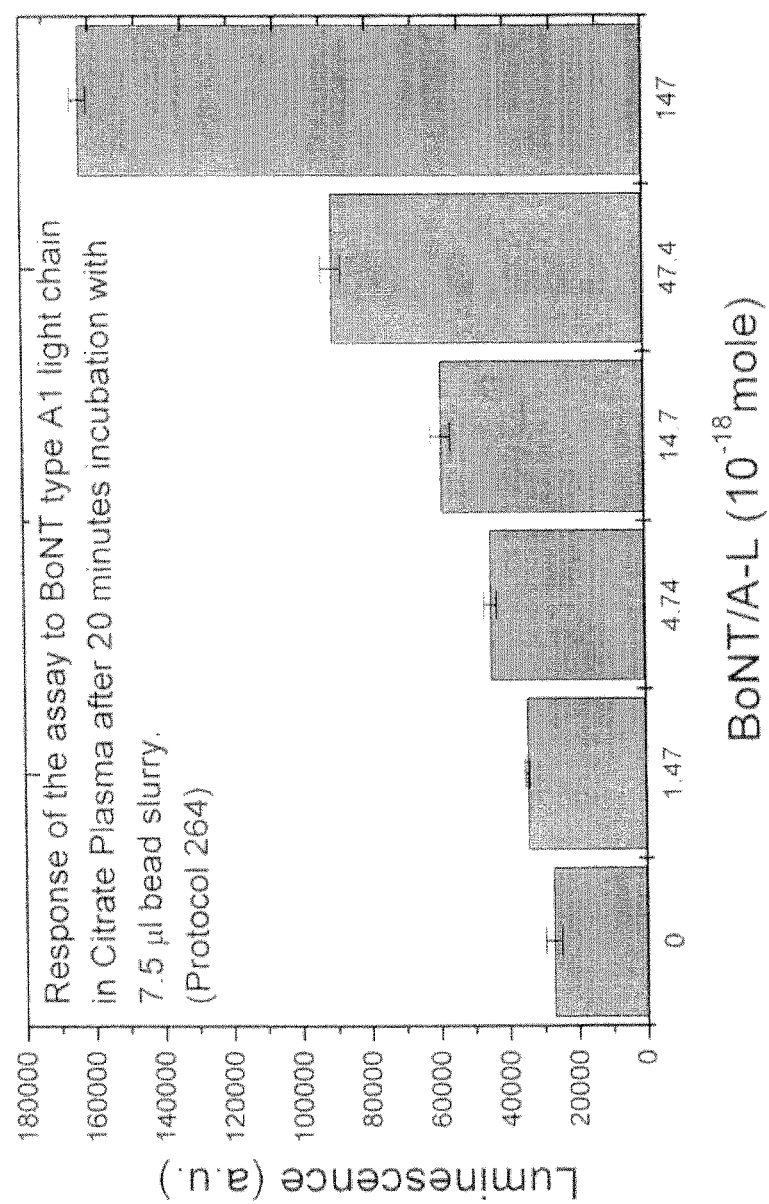

FIG. 12. Response of the assay to various amounts of recombinant BoNT/A-L in citrate plasma. Error bars are the SEM of 6 measurements.

Figure 13:
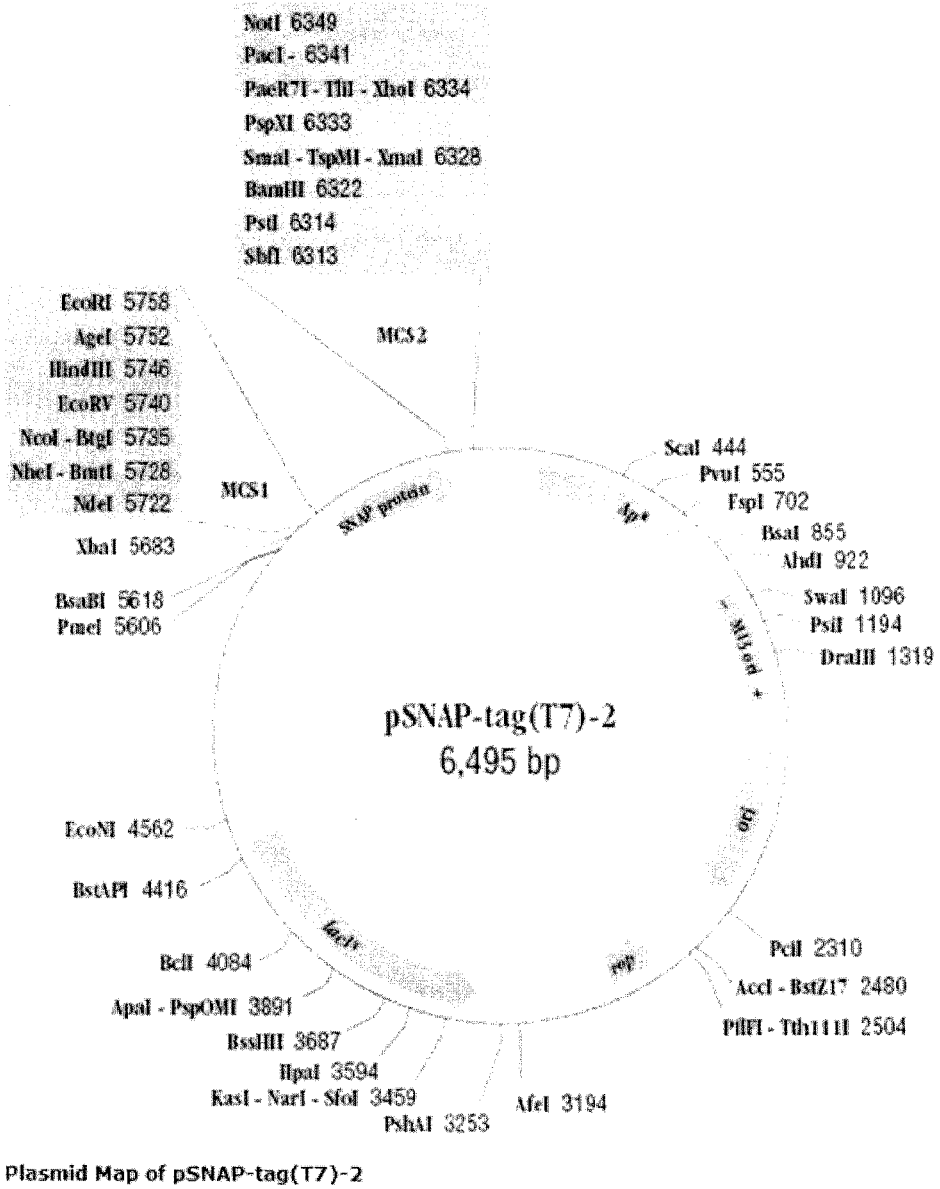

FIG. 13. Plasmid map of pSNAP-tag (T7)-2.

Figure 14:
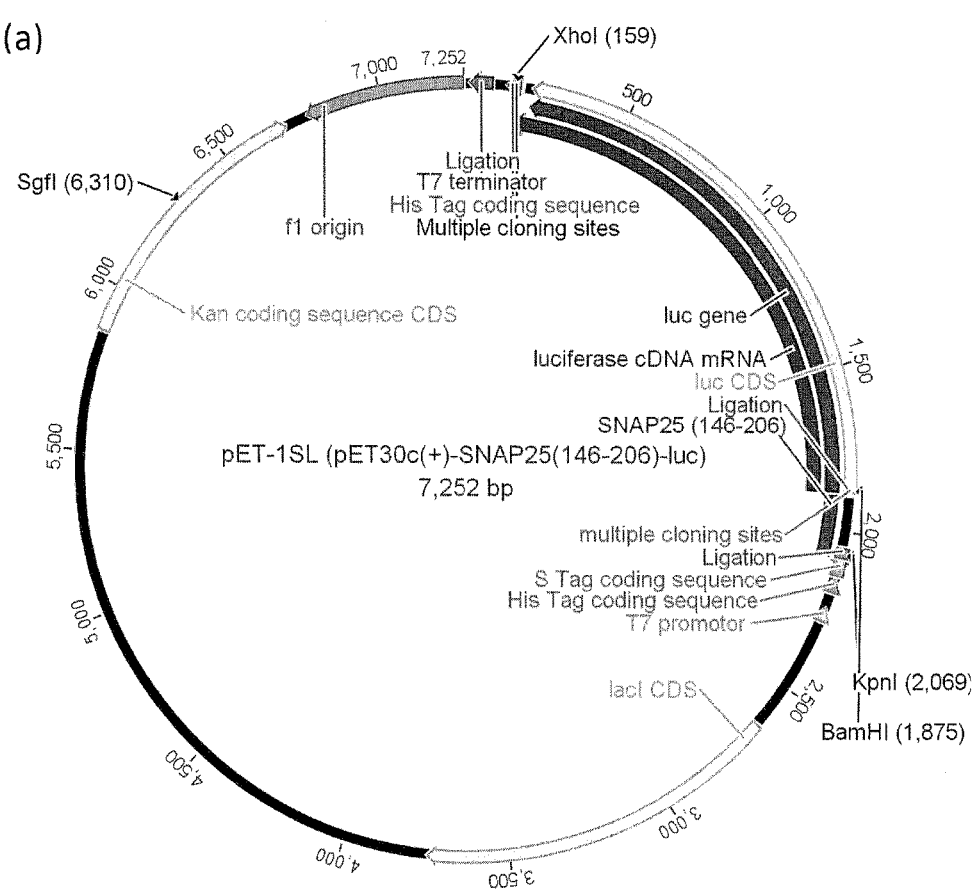

FIG. 14. Restriction digest map of plasmids (a) pET-1SL and (b) pET-2SL showing the location of restriction sites used in constructing the plasmids. These circle maps were generated using Geneious v5.1 (Drummond, Ashton et al. 2010). (c) Gel electrophoresis of plasmids pET-1SL (lanes 1 and 2) and pET-2SL (lanes 3 and 4) after digestion with KpnI/BamHI (lanes 1 and 3) and KpnI/XhoI (lanes 2 and 4). The gel was 1% agarose, stained with 0.5 ug EtBr/ml. Lane 5 was Bench Top 1 kb DNA Ladder G7541 (Promega).

Figure 15:
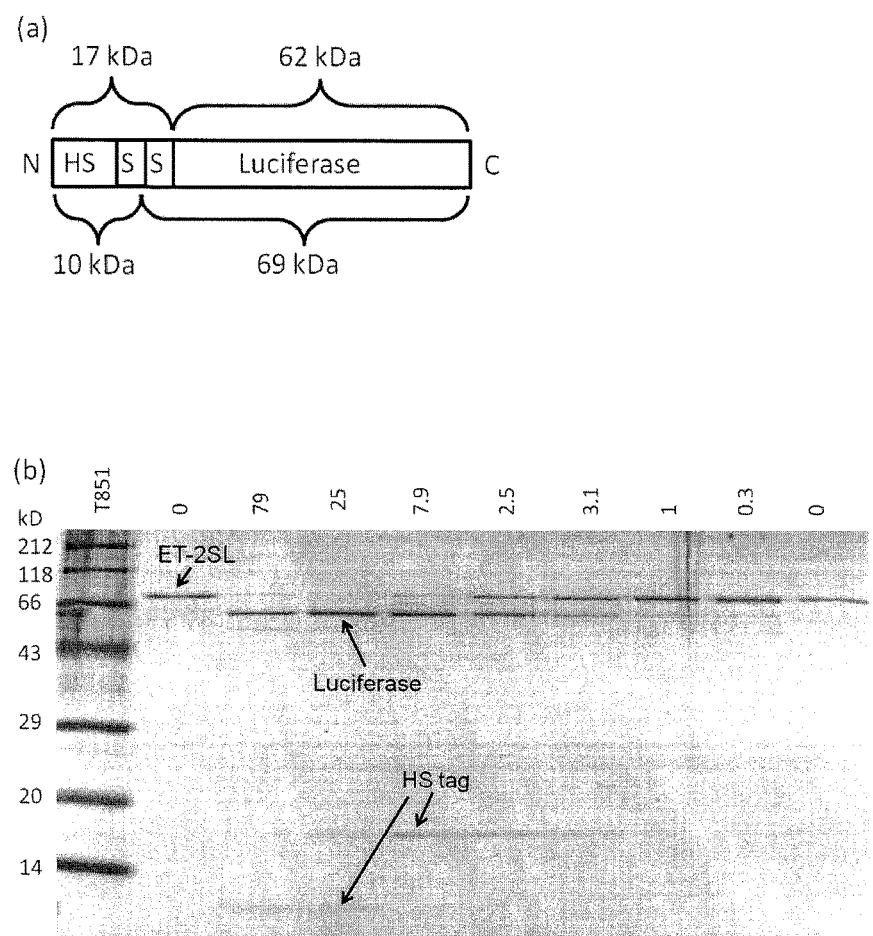
Figure 15:
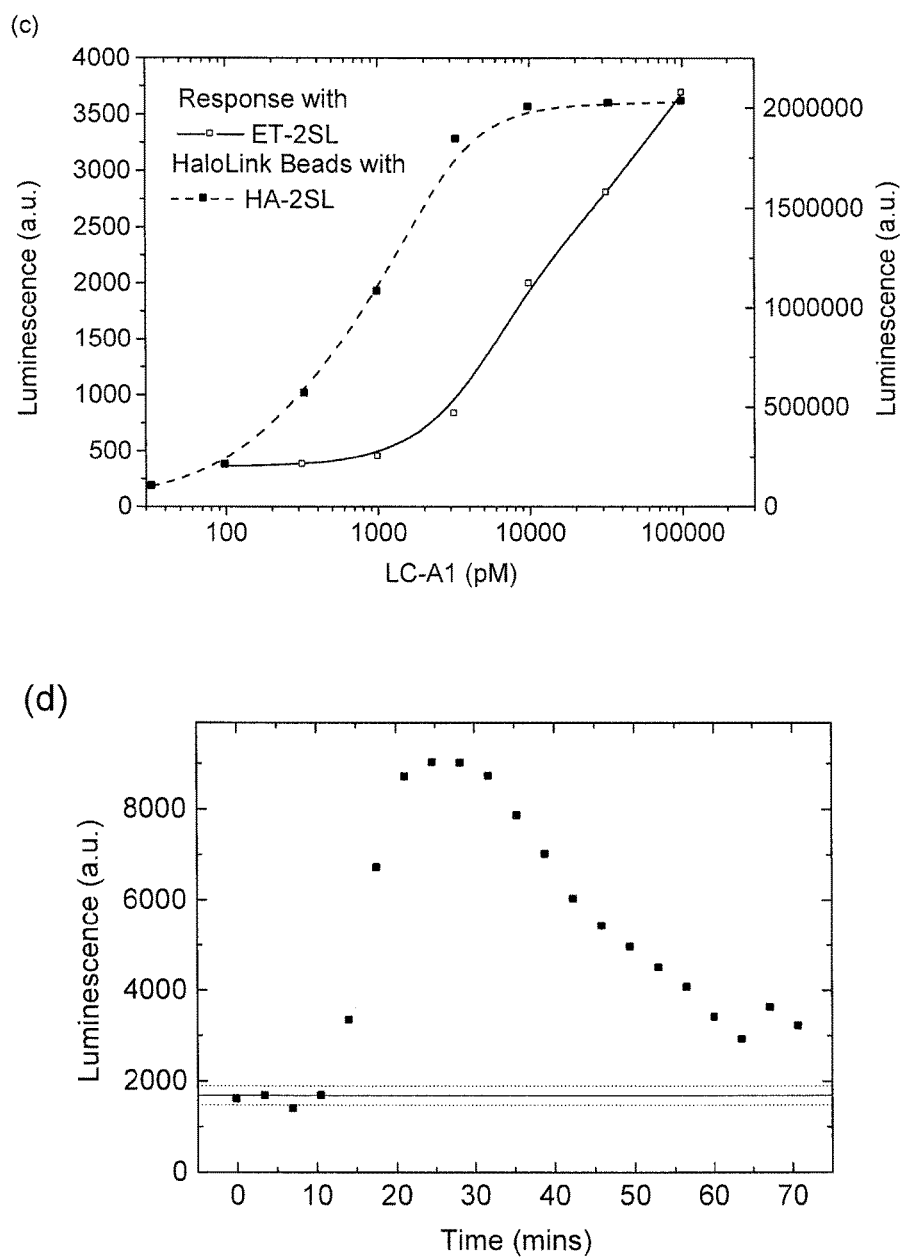

FIG. 15. (a) Fusion protein ET-2SL with a polyhistidine tag and S-Tag (HS) close to the N terminal, a polypeptide linker consisting of two consecutive sequences of Human SNAP-25 amino acids 146-206 (S), and firefly luciferase. Also shown are the expected sizes of products after hydrolysis by LC/A at Gln(197)-Arg(198) of SNAP-25. (b) Reducing SDS PAGE analysis of IMAC purified E. coli lysate containing ET-2SL after 30 mins incubation with LC/A1 at various concentrations. Lanes containing the educt are marked '0' and cleavage products are marked with LC/A1 concentrations in nM above each lane. Marker was Roti-Mark Standard T851 (Carl Roth), 4% stacking gel and 15% resolving gel. (c) Polyhistadine pull-down assay with ET-2SL. Response to LC/A1 in LC/A Hydrolysis Buffer after 20 minutes incubation (left axis). Also shown for comparison is the response of HaloLink Beads loaded with HA-2SL after 20 minutes incubation with recombinant LC/A1 in LC/A Hydrolysis Buffer (right axis). (d) Response of S-protein Agarose with ET-2SL in a micro column (126 µl bed volume and 1.85 mm2 area) to 300 µl 1 nM LC/A1, as a function of time after loading the sample onto the column.

FIG. 16. (a) Restriction digest map of pHA-1S(16-206)L showing the location of restriction sites used in constructing the plasmid. This map was produced with SNAPGENE™ Viewer Version 1.1.2 (GSL Biotech LLC.). (b) Gel electrophoresis of plasmids pHA-1S(16-206)L after digestion with SacI/PmeI (lanes 2 and 3), and SgfI/PmeI (lanes 4 and 5). The gel was 1% agarose, stained with 0.5 µg ethidium bromide/ml. Marker (lane 1) was Bench Top 1 kb DNA Ladder (Promega). (c) Response of HaloLink Magnetic Beads loaded with HA-1S(16-206)L after 60 minutes incubation with LC/A1 in LC/A Hydrolysis Buffer. (d) Normalized response to recombinant LC/A1 of HaloLink Magnetic Beads loaded with HA-1SL, HA-2SL and HA-1S(16-246)L after 60 minutes incubation, fitted with four parameter dose response curves. (n=3, error bars are the standard deviation).

The four parameter EC50 fit to the dose response data in FIGS. 16 (c) and (d), shown above, is given by:

$$\text{Four parameter } EC_{50}(x) = a + \frac{b-a}{1+(x/c)^d},$$

where a is the maximum luminescence, b is the minimum luminescence, c is the EC50 and d is the Hill slope. These are the parameters shown in FIG. 16(c).

Figure 17:
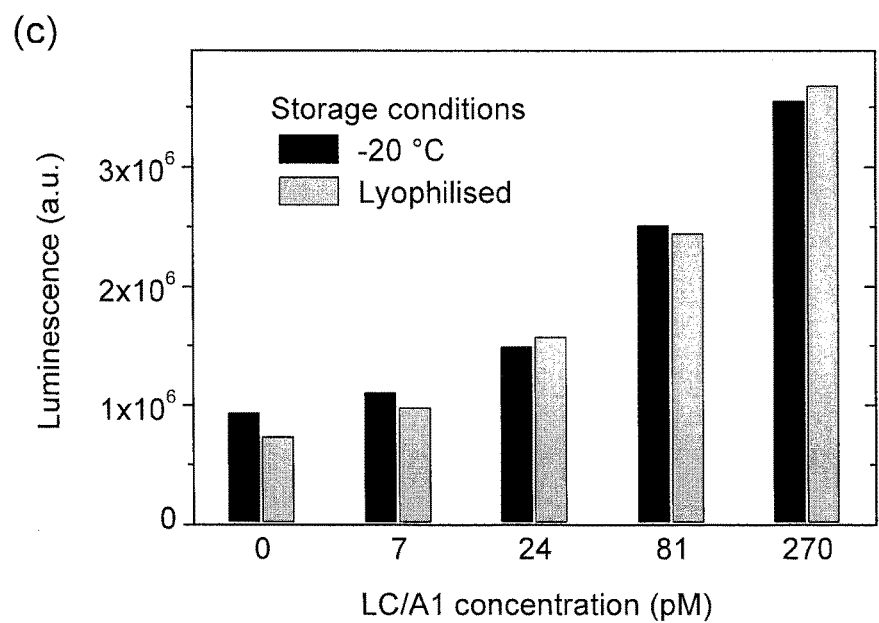

FIG. 17. Effect of incubation time on luminescence response of two batches (A and B) of HaloLink Magnetic Beads loaded with HA-2SL to (a) LC/A Hydrolysis Buffer (blank) and (b) LC/A1 in LC/A Hydrolysis Buffer. The response in (b) is the difference between the response of batch A to 10 pM LC/A1, or batch B to 1 nM LC/A1, and the buffer as shown in (a). A linear fit is shown for the response of batch B to 10 pM LC/A1. Note the different scales for the responses to 10 pM and 1 nM LC/A1. Error bars are the standard deviation (n=6). (c) Comparison of luminescence signal after 20 mins incubation with 0-270 pM LC/A1 from HA-2SL Magnetic Beads after storage at −20° C. in 30% sucrose (black), and after lyophilisation and rehydration (grey). The same batch was used for both experiments.

FIG. 18. Response of HA-2SL activated HaloLink Magnetic Beads to (a) 1 nM LC/A and LC/E in LC/A Hydrolysis Buffer, and 1 nM BoNT/A, B and E and BoNT/A and E complex in Jones Buffer (20 minutes incubation), (b) Clostridium botulinum strains cultured in TPGY media and diluted 1:10 in Jones Buffer (20 minutes incubation, n=2), (c) Dysport in Jones Buffer, 0 (black) and 5 (grey) units after 20 mins incubation, and 0 (black) and 2 (grey) units after 60 mins incubation. The t statistic for the mean luminescence of the analyte and blank is shown above each set (n=6).

Figure 19:
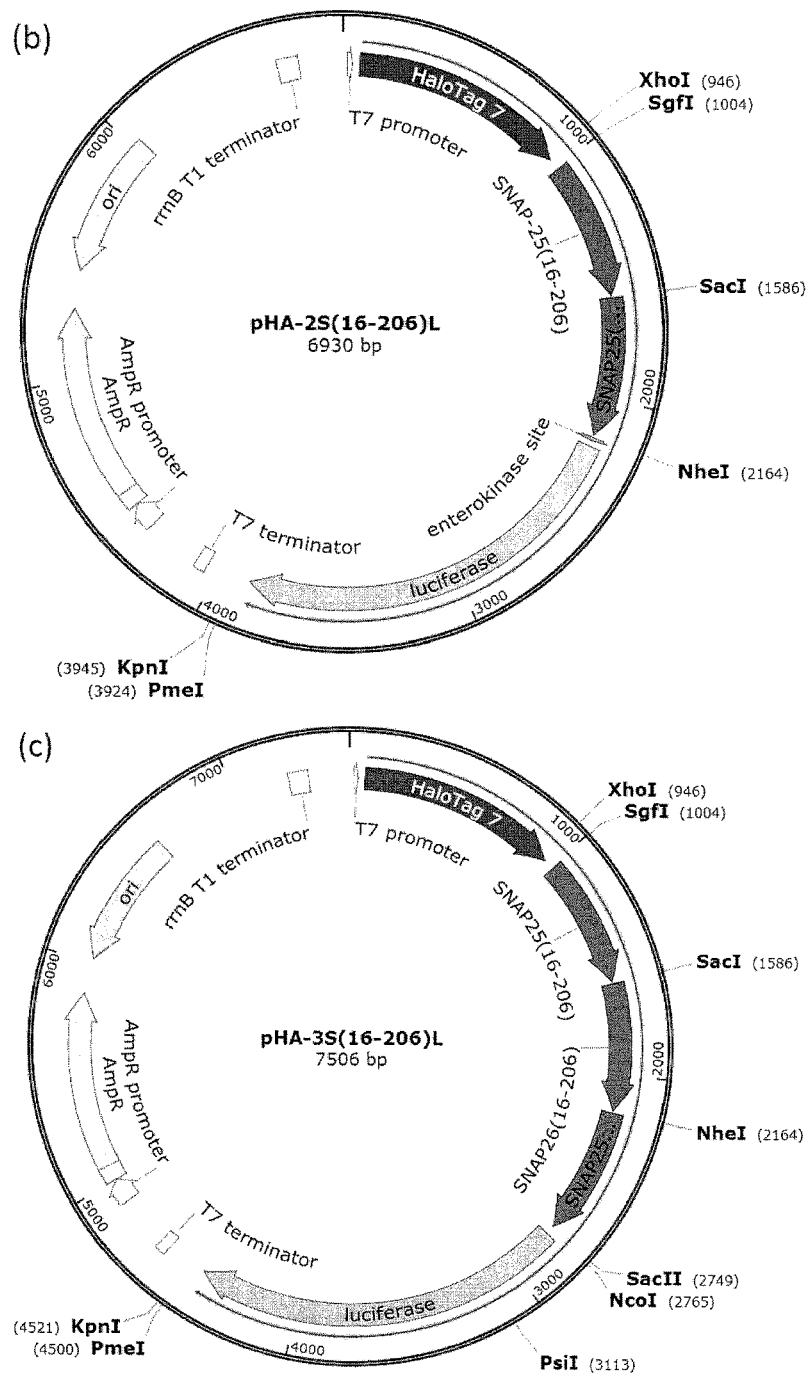

FIG. 19. Restriction digest map of (a) pHA-3SL, (b) pHA-2S(16-206)L and (c) pHA-3S(16-206)L showing the location of restriction sites used in constructing the plasmids. These maps were produced with SNAPGENE™ Viewer Version 1.1.2 (GSL Biotech LLC.).

DETAILED DESCRIPTION OF THE PREFERRED EMBODIMENTS

The Botulinum neurotoxin (BoNT) is a group of toxins which are produced from different strains of the bacteria Clostridium botulinum. Known BoNT types are A, B, C, D, E, F and G. Preferably, the BoNT types in the present invention are type A, C, E, in particular A.

In one embodiment, the peptide referred to in step a) of the method of the invention has an amino acid sequence represented by the following formula (I):

$$TAG-X-REP \quad (I)$$

wherein
TAG is the amino acid sequence of the tag,
X is the amino acid sequence susceptible to proteolytic cleavage by BoNT, and
REP is the amino acid sequence of the reporter domain.

Typically, TAG is at the N-terminus, and REP is at the C-terminus.

The Amino Acid Sequence Susceptible to Proteolytic Cleavage by BoNT

The peptide referred to in step a) of the method of the invention comprises at least one amino acid sequence susceptible to proteolytic cleavage by a BoNT. The amino acid sequence may be cleavable by one of more BoNT types selected from the group consisting of BoNT/A, BoNT/B, BoNT/C, BoNT/D, BoNT/E, BoNT/F, and BoNT/G. Preferably, the peptide is cleavable by BoNT/A. In one embodiment, the peptide is cleavable by BoNT/A, BoNT/C, and BoNT/E. In another embodiment, the peptide is cleavable by BoNT/B, BoNT/D, BoNT/F, and BoNT/G. In three special embodiments, the peptide is cleavable (i) by BoNT/A only, (ii) by BoNT/E only, and (iii) by BoNT types A, B, C, D, E, and F; respectively.

Preferably, the peptide used in step a) of the method of the invention comprises an amino acid sequence susceptible to a proteolytic cleavage by BoNT which comprises the amino acids 152-201 of SNAP25, preferably the amino acids 146-202 of SNAP25, more preferably the amino acid 146-206 of SNAP25, preferably human SNAP25. The amino acid sequence of human SNAP25 is shown in FIG. 4c (SEQ ID NO:1). Preferred, the protein comprises an amino acid sequence of at least two times, preferably two or three times, of the amino acids 152-201 of SNAP25, more preferably the amino acids 146-206 of SNAP25. Preferred, these repetitive amino acids are arranged in series, i.e. without linker amino acids between the sequences.

In one embodiment, the peptide used in step a) of the method of the invention comprises the amino acid sequence as shown in SEQ ID NO:22.

In another embodiment, the peptide used in step a) of the method of the invention comprises the amino acid sequence as shown in SEQ ID NO:23.

In another embodiment, the peptide used in step a) of the method of the invention comprises the amino acid sequence as shown in SEQ ID NO:24.

In another embodiment, the peptide used in step a) of the method of the invention comprises the amino acid sequence as shown in SEQ ID NO:25.

In another embodiment, the peptide used in step a) of the method of the invention comprises the amino acid sequence as shown in SEQ ID NO:26.

In another embodiment, the peptide used in step a) of the method of the invention comprises the amino acid sequence as shown in SEQ ID NO:27.

In another embodiment, the peptide used in step a) of the method of the invention comprises the amino acid sequence as shown in SEQ ID NO:28.

In another embodiment, the peptide used in step a) of the method of the invention comprises the amino acid sequence as shown in SEQ ID NO:26 and the amino acid sequence as shown in SEQ ID NO:28, preferably in series.

In another embodiment, the peptide used in step a) of the method of the invention comprises the amino acid sequence as shown in SEQ ID NO:23 and the amino acid sequence as shown in SEQ ID NO:24, preferably in series.

With reference to formula (I) above, X may comprise, or consist of, amino acids 146-202 of SEQ ID NO:1. In alternative embodiments, X comprises, or consists of, amino acids 146-203, amino acids 146-204, amino acids 146-205, or amino acids 146-206 of SEQ ID NO:1. Preferably, X comprises, or consists of, amino acids 146-206 of SEQ ID NO:1.

It has been found that the sensitivity of the assay is improved if the cleavable sequence is present at least twice within the peptide. Therefore, it is more preferred that X comprises, or consists of, at least two repeats of amino acids 146-202 of SEQ ID NO:1. More preferably, X comprises, or consists of, at least two repeats of amino acids 146-203, of amino acids 146-204, of amino acids 146-205, or of amino acids 146-206 of SEQ ID NO:1. Most preferably, X comprises, or consists of, at least two repeats of amino acids 146-206 of SEQ ID NO:1.

In further preferred embodiments X comprises, or consists of, amino acids 49-202 of SEQ ID NO:1, or amino acids 49-206 of SEQ ID NO:1. More preferably, X comprises, or consists of, at least two repeats of amino acids 49-202, or amino acids 49-206 of SEQ ID NO:1.

In yet other preferred embodiments, X comprises, or consists of, amino acids 35-202 of SEQ ID NO:1, or amino acids 35-206 of SEQ ID NO:1. More preferably, X comprises, or consists of, at least two repeats of amino acids 35-202, or of amino acids 35-206 of SEQ ID NO:1.

In particularly preferred embodiments, X comprises, or consists of, amino acids 21-202 of SEQ ID NO:1, or amino acids 21-206 of SEQ ID NO:1. More preferably, X comprises, or consists of, at least two repeats of amino acids 21-202, or of amino acids 21-206 of SEQ ID NO:1. A very good sensitivity of the assay is obtained for peptides wherein X comprises, or consists of, amino acids 16-202 of SEQ ID NO:1, or preferably amino acids 16-206 of SEQ ID NO:1. Particularly preferred are peptides wherein X comprises, or consists of, at least two repeats of amino acids 16-202 of SEQ ID NO:1, or of amino acids 16-206 of SEQ ID NO:1.

As used herein, the phrase "at least two" preferably means two, three, four or five.

In one embodiment, group X of formula (I) comprises, or consists of, the amino acid sequence as shown in SEQ ID NO:22.

In another embodiment, group X of formula (I) comprises, or consists of, the amino acid sequence as shown in SEQ ID NO:23.

In another embodiment, group X of formula (I) comprises, or consists of, the amino acid sequence as shown in SEQ ID NO:24.

In another embodiment, group X of formula (I) comprises, or consists of, the amino acid sequence as shown in SEQ ID NO:25.

In another embodiment, group X of formula (I) comprises, or consists of, the amino acid sequence as shown in SEQ ID NO:26.

In another embodiment, group X of formula (I) comprises, or consists of, the amino acid sequence as shown in SEQ ID NO:27.

In another embodiment, group X of formula (I) comprises, or consists of, the amino acid sequence as shown in SEQ ID NO:28.

In another embodiment, group X of formula (I) comprises, or consists of, the amino acid sequence as shown in SEQ ID NO:26 and the amino acid sequence as shown in SEQ ID NO:28, preferably in series.

In another embodiment, group X of formula (I) comprises, or consists of, the amino acid sequence as shown in SEQ ID NO:23 and the amino acid sequence as shown in SEQ ID NO:24, preferably in series.

In one embodiment of the invention, the amino acid sequence susceptible for proteolytic cleavage by BoNT comprises the amino acids 1-102 of VAMP2 (vesicle-associated membrane protein 2), preferably human VAMP2, preferably for detecting BoNT types B, D, F and G.

In the following, some exemplary embodiments of the amino acid sequence susceptible to proteolytic cleavage by BoNT (also referred to as "polypeptide linker elements" hereinafter) are described.

2(a) and 2(b) show how SNAP25(146-206) is cleaved by BoNT/A and BoNT/E.

6(a), 6(b) and 6(c) show how SNAP25(16-206) is cleaved by BoNT/A, BoNT/C and BoNT/E.

7 shows how cysteine residues can be deleted from SNAP25(16-206) without affecting the sites required for efficient BoNT/A, C and E recognition and cleavage.

Two or more polypeptide elements in series (e.g. 3, 4 below) interposed between the immobilizing tag (e.g. Halo Tag) and the reporter domain (e.g. firefly luciferase) can be used to create sensitive assays for BoNT types A or E. Assays for each BoNT type may be run in parallel: A positive result for one or more BoNT type shows the presence of those BoNT types in the analyte. Positive results for all assays could indicate the presence of another protease, e.g. trypsin in the analyte.

Two or more polypeptide elements can be combined (e.g. 7 and 9) in series interposed between the Halo Tag and luciferase to provide sensitive assays for BoNT/A, B, C, D, E and F.

9(a), 9(b) and 9(c) show how VAMP2(1-97) is cleaved by BoNT/B, BoNT/D and BoNT/F.

2(a).

Polypeptide linker element for detecting BoNT/A and BoNT/E, but not other BoNT types. Human SNAP-25 amino acids 146-206, with the minimum essential domain for cleavage by BoNT/A (M146-M202) highlighted, and the amino acids (Q197-R198) whose peptide bond is hydrolyzed by BoNT/A shown in bold and underlined.

```
                                                  (SEQ ID NO: 22)
    146            MDENL EQVSGIIGNL RHMALDMGNE IDTQNRQIDR

181  IMEKADSNKT RIDEANQRAT KMLGSG
```

2(b).

Polypeptide linker element for detecting BoNT/A and BoNT/E, but not other BoNT types. Human SNAP-25 amino acids 146-206, with the minimum essential domain for cleavage by BoNT/E (M146-D186) highlighted, and the amino acids (R180-I181) whose peptide bond is hydrolyzed by BoNT/E shown in bold and underlined.

```
                                                  (SEQ ID NO: 22)
    146            MDENL EQVSGIIGNL RHMALDMGNE IDTQNRQIDR

181  IMEKADSNKT RIDEANQRAT KMLGSG
```

In one embodiment of the invention, X comprises, or consists of, SEQ ID NO:22. X may comprise, or consist of, at least two repeats of SEQ ID NO:22. The method in accordance with this embodiment is preferably a method for detecting BoNT/A and BoNT/E, but not other BoNT types.

3.

Polypeptide linker element for detecting BoNT/A, but not other BoNT types. Human SNAP-25 amino acids 146-206, with a point mutation I181E to abolish hydrolysis by BoNT/E is shown underlined. The minimum essential domain for cleavage by BoNT/A ($M^{146}$-$M^{202}$) is highlighted, and the amino acids ($Q^{197}$-$R^{198}$) whose peptide bond is hydrolyzed by BoNT/A are shown in bold and underlined.

```
                                                         (SEQ ID NO: 23)
146                   MDENL EQVSGIIGNL RHMALDMGNE IDTQNRQIDR

181  EMEKADSNKT RIDEANQRAT KMLGSG
```

In one embodiment of the invention, X comprises, or consists of, SEQ ID NO:23. X may comprise, or consist of, at least two repeats of SEQ ID NO:23. The method in accordance with this embodiment is preferably a method for detecting BoNT/A, but not other BoNT types.

4.

Polypeptide linker element for detecting BoNT/E, but not other BoNT types. Human SNAP-25 amino acids 146-206, with a point mutation R198E to abolish hydrolysis by BoNT/A is shown underlined. The minimum essential domain for cleavage by BoNT/E ($M^{146}$-$D^{186}$) is highlighted, and the amino acids ($R^{180}$-$I^{181}$) whose peptide bond is hydrolyzed by BoNT/E are shown in bold and underlined.

6(b).

Polypeptide linker element for detecting BoNT/A, BoNT/C and BoNT/E, but not other BoNT types. Human SNAP-25 amino acids 16-206, with the minimum essential domain for cleavage by BoNT/E ($M^{146}$-$D^{186}$) highlighted, and the amino acids ($R^{180}$-I181) whose peptide bond is hydrolyzed by BoNT/E are shown in bold and underlined.

In one embodiment of the invention, X comprises, or consists of, SEQ ID NO:25. X may comprise, or consist of, at least two repeats of SEQ ID NO:25. The method in accordance with this embodiment is preferably a method for detecting BoNT/A, BoNT/C and BoNT/E, but not other BoNT types.

```
                                                         (SEQ ID NO: 24)
146                   MDENL EQVSGIIGNL RHMALDMGNE IDTQNRQIDR

181  IMEKADSNKT RIDEANQEAT KMLGSG
```

In one embodiment of the invention, X comprises, or consists of, SEQ ID NO:24. X may comprise, or consist of, at least two repeats of SEQ ID NO:24. The method in accordance with this embodiment is preferably a method for detecting BoNT/E, but not other BoNT types.

5.

Amino acid sequence of Human SNAP-25, with amino acids 16-206 highlighted.

```
                                                         (SEQ ID NO: 1)
  1  MAEDADMRNE LEEMQRRADQ LADESLESTR RMLQLVEESK DAGIRTLVML DEQGEQLDRV

61  EEGMNHINQD MKEAEKNLKD LGKCCGLFIC PCNKLKSSDA YKKAWGNNQD GVVASQPARV

121  VDEREQMAIS GGFIRRVTND ARENEMDENL EQVSGIIGNL RHMALDMGNE IDTQNRQIDR

181  IMEKADSNKT RIDEANQRAT KMLGSG
```

6(a).

Polypeptide linker element for detecting BoNT/A, BoNT/C and BoNT/E, but not other BoNT types. Human SNAP-25 amino acids 16-206, with the minimum essential domain for cleavage by BoNT/A ($M^{146}$-$M^{202}$) highlighted, and the amino acids ($Q^{197}$-$R^{198}$) whose peptide bond is hydrolyzed by BoNT/A are shown in bold and underlined.

```
                                                         (SEQ ID NO: 25)
 16                RRADQ LADESLESTR RMLQLVEESK DAGIRTLVML DEQGEQLDRV

61  EEGMNHINQD MKEAEKNLKD LGKCCGLFIC PCNKLKSSDA YKKAWGNNQD GVVASQPARV

121  VDEREQMAIS GGFIRRVTND ARENEMDENL EQVSGIIGNL RHMALDMGNE IDTQNRQIDR

181  IMEKADSNKT RIDEANQRAT KMLGSG
```

```
                                                         (SEQ ID NO: 25)
 16                RRADQ LADESLESTR RMLQLVEESK DAGIRTLVML DEQGEQLDRV

61  EEGMNHINQD MKEAEKNLKD LGKCCGLFIC PCNKLKSSDA YKKAWGNNQD GVVASQPARV
```

```
121  VDEREQMAIS GGFIRRVTND ARENEMDENL EQVSGIIGNL RHMALDMGNE IDTQNRQIDR

181  IMEKADSNKT RIDEANQRAT KMLGSG
```

6(c).

Polypeptide linker element for detecting BoNT/A, BoNT/C and BoNT/E, but not other BoNT types. Human SNAP-25 amino acids 146-206, with the minimum essential domain for cleavage by BoNT/C ($M^{93}$-$D^{202}$) highlighted, and the amino acids ($R^{198}$-$A^{199}$) whose peptide bond is hydrolyzed by BoNT/C are shown in bold and underlined.

```
                                                         (SEQ ID NO: 25)
 16                        RRADQ LADESLESTR RMLQLVEESK DAGIRTLVML DEQGEQLDRV

61  EEGMNHINQD MKEAEKNLKD LGKCCGLFIC PCNKLKSSDA YKKAWGNNQD GVVASQPARV

121  VDEREQMAIS GGFIRRVTND ARENEMDENL EQVSGIIGNL RHMALDMGNE IDTQNRQIDR

181  IMEKADSNKT RIDEANQRAT KMLGSG
```

7.

Polypeptide linker element for detecting BoNT/A, BoNT/C and BoNT/E, but not other BoNT types. Human SNAP-25 amino acids 16-206, with point mutations C84S, C85S, C90S and C92S to abolish disulphide bond formation, are shown underlined. The minimum essential domain for cleavage by BoNT/C ($M^{93}$-$D^{202}$) is shown highlighted, and the amino acids ($R^{198}$-$A^{199}$) whose peptide bond is hydrolyzed by BoNT/C are shown in bold and underlined.

```
                                                         (SEQ ID NO: 26)
 16                        RRADQ LADESLESTR RMLQLVEESK DAGIRTLVML DEQGEQLDRV

61  EEGMNHINQD MKEAEKNLKD LGKSSGLFIS PSNKLKSSDA YKKAWGNNQD GVVASQPARV

121  VDEREQMAIS GGFIRRVTND ARENEMDENL EQVSGIIGNL RHMALDMGNE IDTQNRQIDR

181  IMEKADSNKT RIDEANQRAT KMLGSG
```

In one embodiment of the invention, X comprises, or consists of, SEQ ID NO:26. X may comprise, or consist of, at least two repeats of SEQ ID NO:26.

8.

Amino acid sequence of human VAMP2, with amino acids 1-97 highlighted.

```
                                                         (SEQ ID NO: 27)
  1  MSATAATAPP AAPAGEGGPP APPPNLTSNR RLQQTQAQVD EVVDIMRVNV DKVLERDQKL

61  SELDDRADAL QAGASQFETS AAKLKRKYWW KNLKMMIILG VICAIILIII IVYFST
```

9(a).

Polypeptide linker element for detecting BoNT/B, BoNT/D and BoNT/F, but not BoNT types A, C or E. Human VAMP2 amino acids 1-97, with the minimum essential domain for efficient cleavage by BoNT/B (L60-W90) highlighted, and the amino acids (Q76-F77) whose peptide bond is hydrolyzed by BoNT/B are shown in bold and underlined.

```
                                                         (SEQ ID NO: 28)
  1  MSATAATAPP AAPAGEGGPP APPPNLTSNR RLQQTQAQVD EVVDIMRVNV DKVLERDQKL

61  SELDDRADAL QAGASQFETS AAKLKRKYWW KNLKMMI
```

9(b).

Polypeptide linker element for detecting BoNT/B, BoNT/D and BoNT/F, but not BoNT types A, C or E. Human VAMP2 amino acids 1-97, with the minimum essential domain for efficient cleavage by BoNT/D (Q34-W90) highlighted, and the amino acids (K59-L60) whose peptide bond is hydrolyzed by BoNT/D are shown in bold and underlined.

(SEQ ID NO: 28)
```
  1 MSATAATAPP AAPAGEGGPP APPPNLTSNR RLQQTQAQVD EVVDIMRVNV DKVLERDQKL
 61 SELDDRADAL QAGASQFETS AAKLKRKYWW KNLKMMI
```

9(c).

Polypeptide linker for detecting BoNT/B, BoNT/D and BoNT/F, but not BoNT types A, C or E. Human VAMP2 amino acids 1-97, with the minimum essential domain for efficient cleavage by BoNT/F (S28-W90) highlighted, and the amino acids (Q58-K59) whose peptide bond is hydrolyzed by BoNT/F are shown in bold and underlined.

(SEQ ID NO: 28)
```
  1 MSATAATAPP AAPAGEGGPP APPPNLTSNR RLQQTQAQVD EVVDIMRVNV DKVLERDQKL
 61 SELDDRADAL QAGASQFETS AAKLKRKYWW KNLKMMI
```

In one embodiment of the invention, X comprises, or consists of, SEQ ID NO:28. X may comprise, or consist of, at least two repeats of SEQ ID NO:28. The method according to this embodiment is preferably a method for detecting BoNT/B, BoNT/D and BoNT/F, but not BoNT types A, C or E.

Reporter Domain

The peptide further comprises the amino acid sequence of a reporter domain. The reporter domain preferably is a fluorescent polypeptide or a bioluminescent polypeptide. Fluorescent polypeptides include, but are not limited to, Green Fluorescent Protein (GFP), Yellow Fluorescent Protein (YFP) or the like. Preferably, the reporter domain is a bioluminescent polypeptide, more preferably luciferase or a luminescent derivative thereof. Preferably, the luciferase is firefly luciferase, e.g. East European firefly luciferase (EC1.13.12.7) from photinus pyralis. The amino acid sequence of luciferase is known in the art.

Tag and Support

The peptide used in the method of the invention further comprises a tag suitable for attaching said peptide to a support. The tag is an immobilization domain which can serve to attach the peptide to a solid support. Suitable tags are known in the art and include, but are not limited to, hexahistidine tag, S-tag, Halo-tag and a SNAP-tag. The attachment of the tag to the support can be effected via non-covalent bonds or via covalent bonds. A non-covalent tag is for example the hexahistidine tag. A tag for covalent attachment is for example the Halo-tag, e.g. the tag as described in U.S. Pat. No. 8,202,700 B2, U.S. Pat. No. 7,429,472 B2 or Los et al. (2008) ACS Chemical Biology 3(6): 373-382, the disclosure of which is incorporated herein by reference. Another tag for covalent attachment is the SNAP tag.

According to the present invention it is preferred that the peptide is attached to the support via covalent bonds, more preferably via a Halo-tag. Preferred tags are those that provide covalent or covalent-like binding of the polypeptide linker to the solid support.

With reference to formula (I) above, TAG preferably comprises a Halo-tag, i.e. an amino acid sequence of a genetically modified Rhodococcus haloalkane dehalogenase, preferably as described in U.S. Pat. No. 8,202,700 B2, U.S. Pat. No. 7,429,472 B2 or Los et al. (2008) ACS Chemical Biology 3(6): 373-382. In one embodiment, TAG comprises Rhodococcus haloalkane dehalogenase with a His272Phe mutation. It is further possible that TAG comprises a linker sequence separating the Rhodococcus haloalkane dehalogenase from group X. The linker sequence typically consists of 10 to about 100 amino acids, preferably of 10 to about 20 amino acids.

Suitable supports include, but are not limited to, microchips, e.g. lab on a chip, or beads (magnetic or non-magnetic), preferably magnetic beads. The chips or the magnetic or non-magnetic beads have to be covered by suitable agents in order to bind to the specific tag used. Magnetic beads which can be used to attach a peptide carrying a Halo-tag or a SNAP-tag are known in the art and are commercially available, e.g. HaloLink magnetic beads from Promega (G9311) or SNAP-Capture magnetic beads, available by New England Biolabs (S9145S).

In step b) of the method of the invention, the peptide of step a) is attached to the support, e.g. the magnetic or non-magnetic beads or the microchip. The conditions suitable to provide a sufficient attaching of the peptide via the tag to the support are known in the art and typically depend on the specific tag used. Optionally, unbound peptides, i.e. peptides which do not attach to the support, can be removed, e.g. by rinsing, e.g. by use of a magnet to attract the magnetic beads, or a centrifugal device or gravity when using non-magnetic beads.

In step c), the test sample to be investigated for the presence or amount of BoNT is added to the support with the attached peptide, typically under condition suitable to enable a proteolytic cleavage of the BoNT present in the test sample. After sufficient time in order to allow proteolytic activity of BoNT preferably the magnetic beads, when used as support, are removed with the aid of a magnet in order to remove uncleaved peptides.

In step d) of the invention, the luminescence signal of the luciferase cleavage product is determined. That is, the amount of luciferase obtained by cleaving the peptide of the invention at the amino acid sequence susceptible for proteolytic cleavage by BoNT is measured. Suitable conditions to determine the amount of luciferase by luminescence signals are known in the art. Form the luminescence signal, the presence and amount of BoNT in the test sample can be determined.

In a preferred embodiment of the invention, the peptide to be used in the method of the invention comprises a Halo-tag, two times the amino acids 146-202 of SNAP25, preferably two times the amino acids 146-206 of SNAP25, preferably human SNAP25, as well as the amino acid sequence of luciferase in series. In another preferred embodiment of the invention, the peptide to be used in the method of the invention comprises a Halo-tag, once or twice the amino acids 16-206 of SNAP25, preferably of human SNAP25, as well as the amino acid sequence of luciferase in series.

The test sample to be investigated for presence or amount of BoNT can be in form of any liquid, e.g. obtained from a beverage or food, but is preferably a blood sample.

The present invention further relates to a peptide comprising an amino acid sequence susceptible to proteolytic cleavage by BoNT comprising an Halo-tag, two times the amino acids 152-201 of SNAP, preferably two times the amino acids 146-206 of SNAP25, preferably human SNAP25, as well as the amino acid sequence of luciferase in series.

EXAMPLES

Example 1

I. Abstract

Described here is a new assay for rapid, sensitive detection of the toxin that causes botulism: Botulinum Neurotoxin (BoNT) from the bacteria *Clostridium botulinum*. The assay was specifically designed for finding traces of BoNT in blood samples for bio-defence applications, but it could also be useful for confirming cases of food, wound or infant botulism. The assay can sense as little as 1.5 attomoles BoNT type A light chain in a 5 µl sample of blood serum in half an hour. Also demonstrated is the ability to detect toxin from *Clostridium botulinum* serotype A. The assay can distinguish between a blank and BoNT type A light chain at a concentration of 160 fM in a 400 µl sample volume. Thus, the sensitivity of the assay is close to that of the standard mouse bioassay. The assay is also designed for detecting BoNT types C and E, and it is planned to extend the assay for detecting types B, D, F and G as well, so that it would in principle be possible to detect any type of BoNT in one test. The sensitivity and speed of the assay, combined with its potential to be automated for use in the field should make it useful for bio-defence applications.

II. The Need for a Sensitive, Rapid Blood Test for Bio-Defence

Botulism is a deadly disease caused by Botulinum Neurotoxin (BoNT), which is produced by the anaerobe *Clostridium botulinum*. BoNT can enter the body orally via tainted food or drink, or through breathing an aerosol containing the toxin, which is of particular concern for bio-defence. Other types are wound botulism, when the bacteria or spores enter through a wound and the toxin is then produced inside the body, and infant botulism, which occurs when the bacteria, or bacterial spores, enter the gastro-intestinal tract of an infant, or in rare cases, that of an adult.

There are seven known serotypes of the bacteria, which produce seven types of BoNT, labeled A to G. All are highly toxic, but those that commonly affect humans are types A, B and E. The bacteria that produce BoNT are ubiquitous in soil and therefore are easy to obtain, and also to grow under fairly simple conditions. The high toxicity and relative ease of obtaining and spreading the toxin raise concerns that the BoNT may be used in a terrorist attack (Woods 2005).

BoNT produces disease by preventing the release of acetylcholine from presynaptic neurons to postsynaptic neurons. Therefore nerve impulses are stopped, resulting in a flaccid paralysis. The incubation period before symptoms become apparent can be as brief as 24 to 36 hours from the time of intoxication.

Treatment with the antitoxin should be done as soon as possible, preferably before the onset of clinical signs because the antitoxin doesn't work as well after the onset of symptoms. According to the former commander of the United States Army Medical Research Institute for infectious diseases (USAMRIID) Col (ret) David Franz, DVM, PhD: "A successful attack with BoNT in aerosol could actually overcome the health care providing facilities of a city because anyone who doesn't receive antitoxin in a timely manner is going to need a ventilator."

As far as is known the toxin is tasteless and odourless, so an attack may go unnoticed until clinical symptoms become apparent in some of the victims. In such an event prompt treatment with anti-toxin would be required, so it is vital that the toxin be rapidly detected if an attack is suspected.

Detection of *Clostridium botulinum* Neurotoxin (BoNT) in blood is challenging because it is the most lethal toxin known (Woods 2005) and therefore a test for it must be highly sensitive. The LD 50 of BoNT is about 1 ng/kg body weight, and the infective dose by inhalation of an aerosol may be as little as 3 ng/kg body weight (Woods 2005). The standard mouse bioassay for the toxin has a detection limit of 5-10 pg (Ferreira, Eliasberg et al. 2001). The assay requires intraperitoneal injection of two or more 20-30 g mice with 0.4 ml of serum, or other sample, and watching for signs of intoxication. Mice intoxicated with BoNT will usually die within 6-24 hours depending on the level of toxin in the sample (CDC 1998). Immunoassays for BoNT, such as ELISA, can be performed more rapidly than the mouse bioassay, but these can take several hours to complete, depending on the concentration of the toxin. So this rapid, sensitive assay has been developed for bio-defence applications.

III. Principle of the Assay

Figure 1:
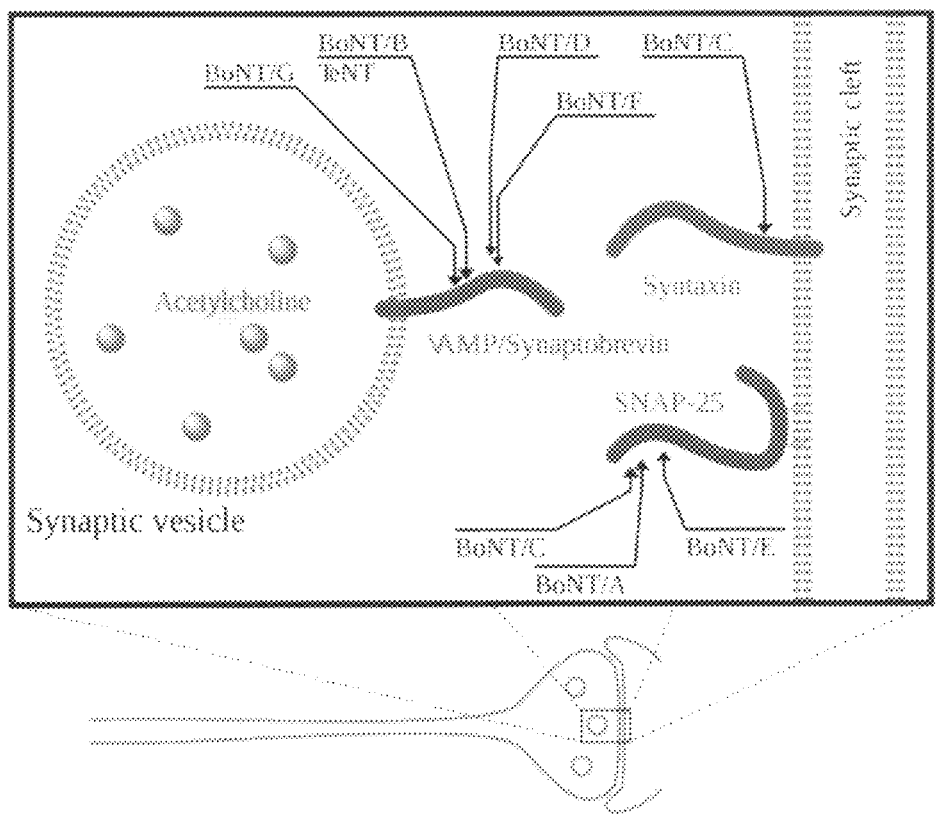
FIG. 1. Cartoon of the cutting sites of BoNT (and also Tetanus Neurotoxin) on the peptides VAMP/Synaptobrevin, SNAP-25 and Syntaxin, that make up the SNARE complex of neurons. These peptides are shown attached to or embedded in lipid bilayers of the neuron. Illustration from Wikipedia.

Once BoNT gains entry to the neuron, it dissociates into two parts, called the heavy and light chains. The light chain prevents release of acetylcholine by cleaving part of the neuronal SNARE protein. As shown in FIG. 1, different serotypes affect different parts of the SNARE complex.

Figure 2:
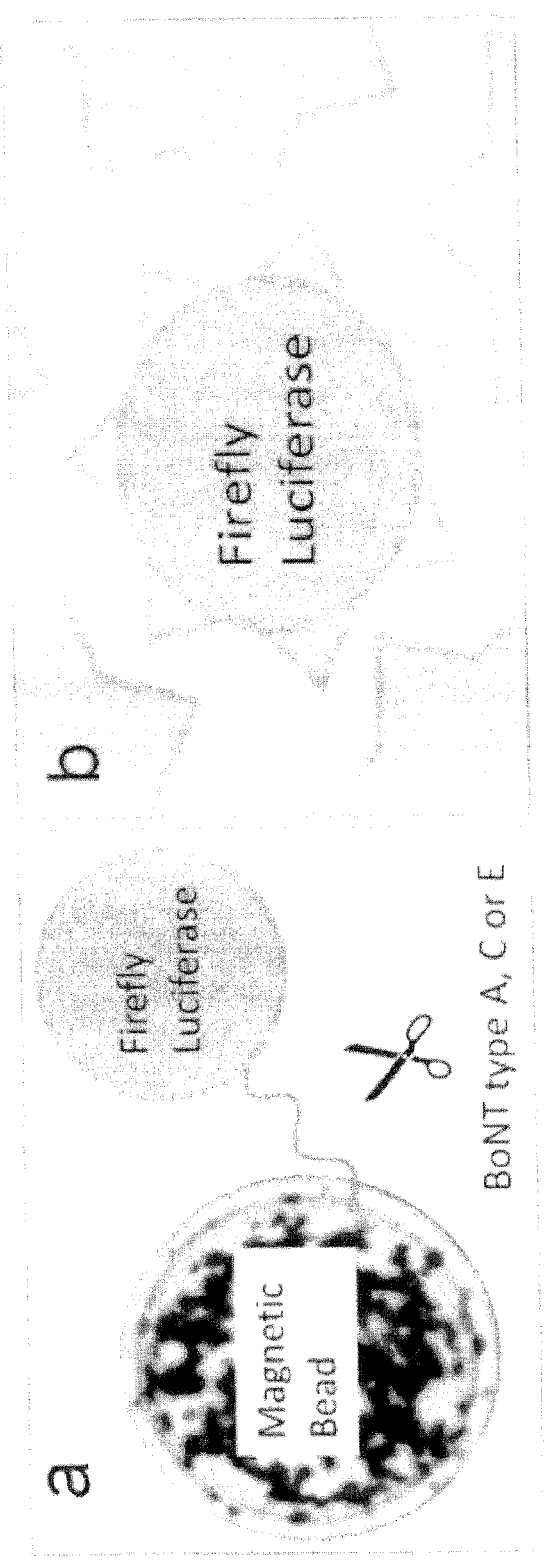
FIG. 2.

The assay described here is designed to detect proteolytic activity of BoNT types A, C and E. Modification of the existing assay could in principle allow for detection of all types (A-G). The principle of the assay is shown schematically in FIG. 2. Firefly luciferase is tethered to magnetic beads with a peptide that is susceptible to proteolytic cleavage by BoNT types A, C and E, FIG. 2 (*a*). This peptide consists of one or more cutting and recognition sequences of human SNAP-25 (amino acids 146-206).

After allowing time for cleavage of the peptide by BoNT, the magnetic beads are removed with the aid of a magnet and luciferin substrate is added to the remaining liquid. Each released luciferase molecule activates multiple substrate molecules to provide a large luminescence signal, FIG. 2 (*b*).

The magnetic beads used in the assay are HaloLink Magnetic Beads from Promega (Product number G9311). They consist of agarose beads containing paramagnetic iron oxide. A microscope image of the beads, which have diameters ranging from 10 to 100 microns, is shown in FIG. 3. The iron oxide which gives the beads a dark grey appearance can be seen inside the beads.

III. Design of the Recombinant Protein for Coating Magnetic Beads

The proteins for coating the magnetic beads are produced by bacterial expression in *Escherichia Coli*. The *E. coli* has been transformed with plasmids pHA-1SL or pHA-2SL, restriction maps of which are shown in FIG. 4. These plasmids are a based on the plasmid pFN18A (Product number G2751) from Promega, which contains a coding region for the HaloTag. The Halo-tag is a 34 kDa monomeric derivative of dehalogenase. The Halo-tag covalently binds to synthetic ligands comprising a chloroalkane linker attached to a solid surface (Los, Encell et al. 2008). Inserted into this plasmid downstream from the coding region for the HaloTag is a region encoding one or two cutting and recognition sequences of human SNAP 25 (amino acids 146-206), followed by a region encoding luciferase. It is planned that a plasmid encoding three SNAP-25 sequences in this region will also be constructed. The reason for using amino acids 146-206 of human SNAP-25 as the cutting and recognition sequence is that this region has extensive contacts to binding sites on BoNT/A-L (Breidenbach and Brunger 2004). The schematic diagram shown in FIG. 5 shows the extensive contacts between human SNAP-25 residues 152-201 and binding sites on BoNT/A-L. This suggests that in order to obtain efficient cleavage it would be prudent to use as much as possible of the SNAP-25 sequence shown in FIG. 5.

IV. Methods, Results, Discussion

Figure 4B:
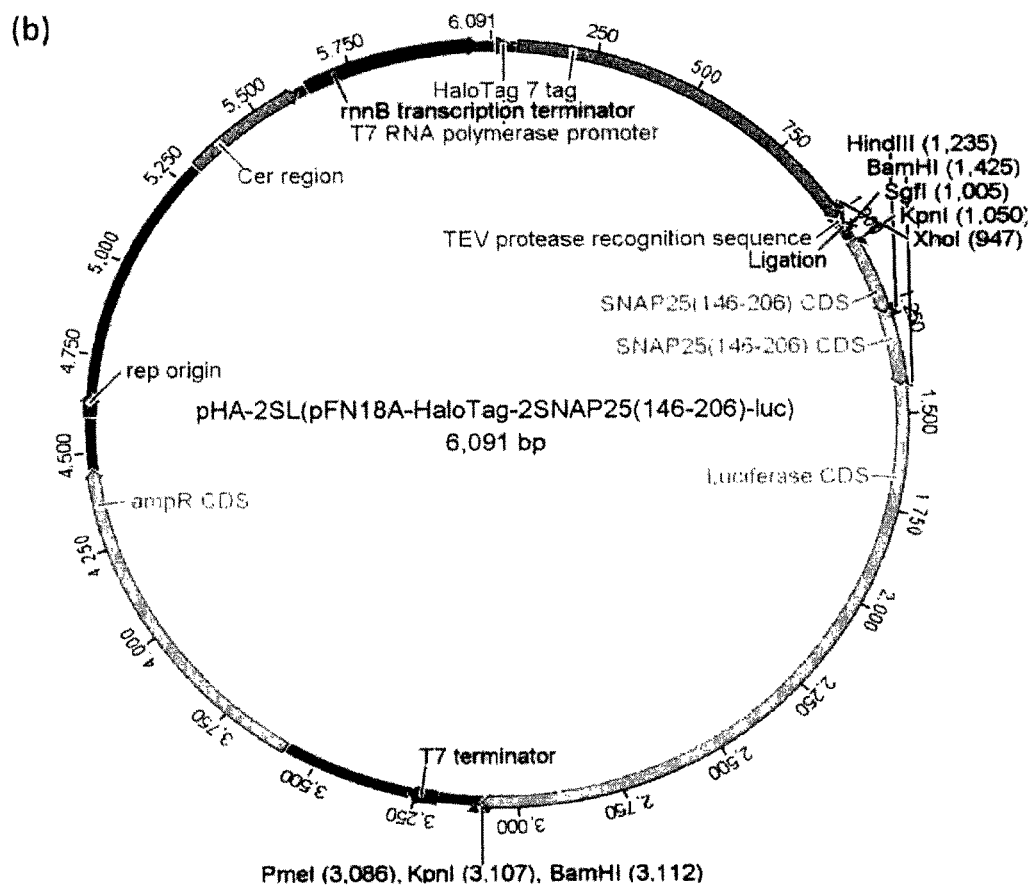
Figure 4C:
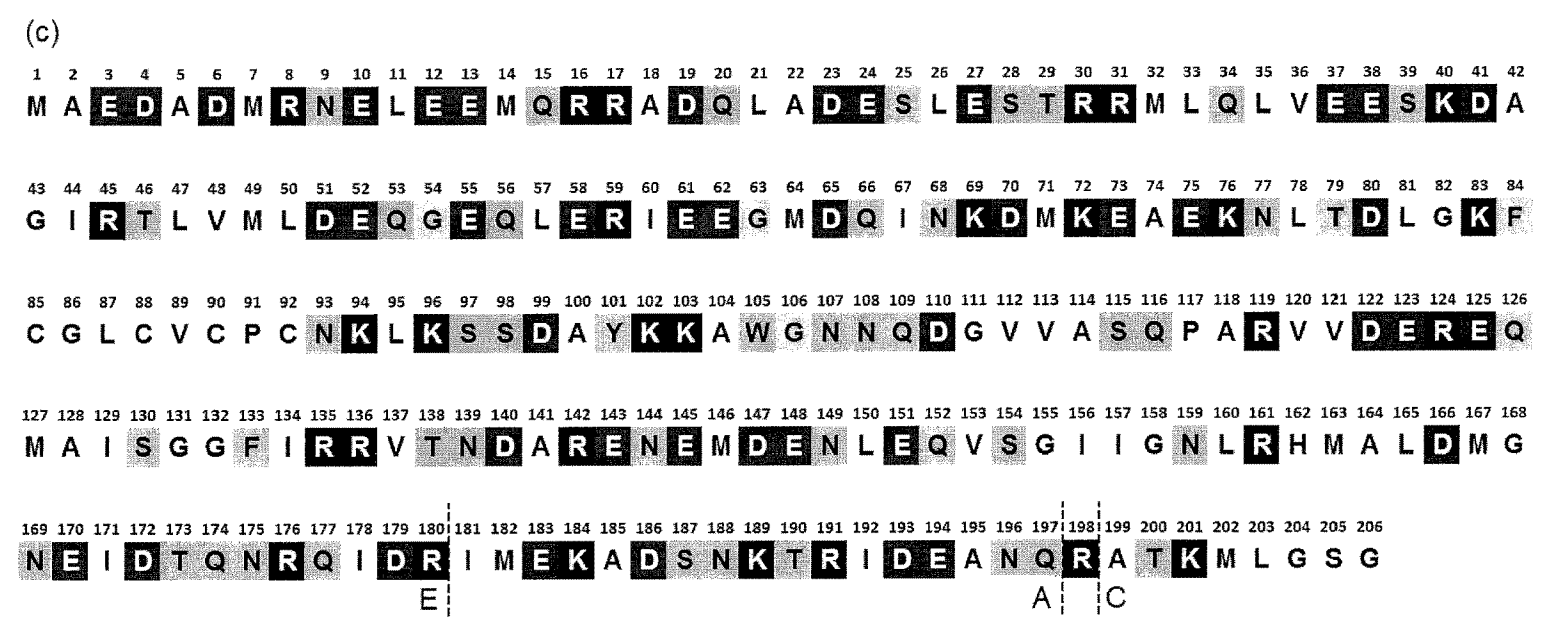

The plasmids pHA-1SL and pHA2SL were constructed using standard methods of genetic engineering (see Appendix A). The plasmids were purified from cell cultures and then digested with SgfI and PmeI restriction enzymes. The digestion products were analyzed by gel electrophoresis. FIG. 6 shows the digestion products in lanes marked '1a' and '1 b', from cells expected to contain pHA-1SL. These bands are close to the expected sizes of the digestion products of pHA-1SL: 1892 and 4010 bp, as can be seen in the restriction map in FIG. 4(a). Digestion products in lane '2b', from cells expected to contain pHA-2SL, have bands close to sizes of digestion products as seen in FIG. 4(b): 2081 and 4010 bp. Thus cells used to produce the plasmid in lane 1a were cultured for expression of pHA-1SL, and cells used to produce the plasmid in lane 2b were cultured for expression of pHA-2SL.

Cells were pelleted and stored at −80 C. Cell pellets were thawed and lysed by incubation for 30 minutes in buffer containing lysozyme and DNase I. Cell lysate was clarified by centrifugation at 24,000 r.c.f. for 5 minutes. HaloLink beads were incubated with clarified cell lysate for 1 hour at room temperature. Beads were washed in buffer and stored at −20 C in buffer containing 30% sucrose.

Beads coated with the protein were thawed and 7.5 µl bead slurry was incubated with 4.7 µl LcA Hydrolysis Buffer (200 mM HEPES, 0.5 mg/ml BSA, pH 8.2, 0.01% IGEPAL CA-630) spiked with recombinant BoNT type A light chain (BoNT/A-L) for 20 minutes. The beads were removed with the aid of a magnet, and the presence of released luciferase was detected by measuring the luminescence after addition of 25 µl Bright-Glo Luciferase Assay (Promega). The results of the assay for proteins with one (pHA-1SL) and two (pHA-25L) SNAP25 sequences (amino acids 146-206) are shown on the same graph for comparison, in FIG. 7.

These results show that the peptide with two cutting and recognition sequences in the cleavable peptide provides a more sensitive assay than the peptide with one cutting and recognition sequence. This might be due to three-dimensional hindrance by the luciferase or Halo-tag to efficient substrate recognition by BoNT/A-L, which requires binding at specific sites on BoNT/A-L. Thus, the use of two cutting and recognition sequences is essential to the sensitivity of the assay. The trend shown in FIG. 7 suggests that it may be possible to improve the sensitivity of the assay further by including more cutting and recognition sequences in the cleavable peptide.

The sensitivity of the assay was also compared in to a commercially available assay for BoNT/A called SNAPtide #521 (List Biological Laboratories). This is a synthetic peptide containing the natural cleavage site of SNAP25 flanked on either side by a fluorophore and a chromophore. When the fluorophore (flurorescein-thiocarbomoyl (FITC)) of intact SNAPtide #521 is excited with light, energy absorbed is transferred non-radiatively to the chromophore (4-(dimethylamino)phenyl)azo)benzoic acid (DABCYL)) by Foerster Resonance Energy Transfer (FRET), thereby quenching fluorescence. When the peptide linker is cleaved by BoNT/A-L, FRET is disrupted and the fluorophore emits a fluorescence signal.

The response of SNAPtide #521 to BoNT/A-L (FIG. 7) has a larger background signal than that of the luminescence-based assays. This background fluorescence is due to inefficient quenching by FRET of intact SNAPtide #521. Above 10000 $10^{-18}$ moles BoNT/A-L the fluorescence signal increases with increasing BoNT/A-L. The increase in fluorescence is due to cleavage of the peptide linker between the fluorophore and the chromophore of SNAPtide #521, providing measurable amounts of free fluorophore, and thus a reduction in quenching by FRET.

Both luminescence-based assays are significantly more sensitive to BoNT/A-L than SNAPtide #521. The extra sensitivity is probably due to the use of the full recognition sequence (SNAP-25 amino acids 146-206) (Dong, Tepp et al. 2004). The reliance by SNAPtide #521 on FRET between the chromophore and fluorophore, which are tethered by a cleavable linker, limits the length of the cutting and recognition sequence to a maximum of about 13 amino acids. This seems to place a limit on the sensitivity, or a requirement for long incubation times (Ruge, Dunning et al. 2011), for FRET-based assays.

From now on the discussion will focus on the assay with two SNAP-25 sequences in the cleavable peptide. To confirm that this peptide was cleavable by BoNT/A, protein containing luciferase was purified from clarified cell lysate by size exclusion chromatography and incubated with recombinant BoNT/A-L for 30 minutes. The digestion products were analyzed by SDS-PAGE, shown in FIG. 8. The lane marked 'control' has a band with an expected size of 112 kDa. This band is absent in the lane marked '+BoNT/A-L' and instead there are two bands, corresponding to digestion products of the HaloTag (43 kDa) and luciferase (69 kDa). Thus the protein is cleaved as expected by recombinant BoNT/A-L.

The Western Blot results confirm the conclusions from the SDS PAGE analysis and are consistent with the following:
 The protein HA-2SL has a predicted size of 112 kD.
 BoNT/A light chain cleaves SNAP25 sequences between amino acids Q and RAT.
 After cleavage at the first site, products will have sizes of 43 and 69 kD. The 43 kD piece contains HaloTag and the 69 kD contains luciferase.
 After cleavage at the second site, products will have sizes of 50 and 62 kD. The 50 kD piece contains HaloTag, and the 62 kD piece contains luciferase.
 Bands at 50 and 62 kD are more prominent than those at 43 and 69 kD, indicating that the second site is cleaved more than the first cleavage site.

The response of the assay to recombinant BoNT/A-L in LcA Hydrolysis Buffer is shown in FIG. 9. This figure shows inter assay variation of the blank signal, which may be due in part to variations in the number of beads used in each assay. There is clearly a response above the blank in the presence of $1.47 \times 10^{-18}$ moles BoNT/A-L. One ng of *Clostridium botulinum* type A toxin contains $6.7 \times 10^{-15}$ moles BoNT/A-L, so the assay should be able to detect as little as $2.2 \times 10^{-1}$ pg of BoNT/A. The sensitivity of the mouse bioassay to BoNT/A is 5-10 pg ($3.32$-$6.64 \times 10^{-17}$ moles) (Ferreira, Eliasberg et al. 2001). Thus although the assay can detect less total BoNT/A than the mouse bioassay, the mouse bioassay uses a sample volume of 400-500 µl, whereas the sample volume for this assay is 5 µl. Therefore testing of this assay with 400-500 µl sample volume is needed in order to properly compare the sensitivity of this assay with the mouse bioassay.

To compare this assay with the mouse bioassay, 15 µl bead slurry was incubated for 20 minutes with 400 µl LcA Hydrolysis Buffer spiked with 10 pg BoNT/A-L. This concentration is close to the limit of detection of the standard mouse bioassay (Ferreira, Eliasberg et al. 2001). The response, FIG. 10, shows the assay can be used to distinguish a concentration of BoNT/A-L from the blank with 99% confidence. The lines on the graph of FIG. 10 represent the 99% confidence level of a single tailed t-distribution of the luminescence. These levels are 3.365 times the Standard Error of the Mean (SEM) above the sample mean luminescence signals of buffers without BoNT/A-L, and 3.365 times the SEM below the sample mean response for 160 fM recombinant BoNT/A-L. This definition is consistent with that of the minimum detectable dose ($y_{min}$) of Rodbard: for an unknown analysed $n_2$ times the minimum detectable dose is given by:

$$y_{min} = \overline{y_2} = \overline{y_1} + ts\left[\frac{1}{n_1} + \frac{1}{n_2}\right]^{1/2}$$

where t is the percentile limit of detection, s is the sample standard deviation, $n_1$ the number of blank samples analysed and $y_1$ is the mean of the blank (Rodbard 1978). Although there is a relatively high background, the assay has a sensitivity approaching that of the standard mouse bioassay.

To check that the assay is sensitive to the toxin from *Clostridium botulinum* serotype A, and not just recombinant BoNT/A-L, the assay was challenged with BTA Reduction Buffer (20 mM HEPES, pH 8.0, 5 mM DTT, 0.3 mM $ZnCl_2$, 0.2% Tween 20) spiked with 5 Units Dysport (abobotulinum toxin-A). The results of this experiment are shown in FIG. 11. These results show that the assay is responsive to as little as 5 units of Dysport. Unfortunately there is no clear relationship between Units of Dysport and BoNT/A concentration, so it is not possible to state the amount of BoNT in the sample. However, the active ingredient in Dysport, and a similar product called Botox, is toxin from *Clostridium botulinum* serotype A. (A major difference between Dysport and Botox is the hemagglutinin complex, which gives rise to differences in the dose. One unit of onabotulinum-toxin A from Botox is equivalent to about 2.75 units of abobotulinum toxin-A from Dysport [4]).

As the assay will be used for detecting traces of BoNT/A in blood plasma, it was tested with citrate plasma spiked with recombinant BoNT/A. FIG. 12 shows the response in citrate plasma. As expected, the luminescence signal increases as the amount of BoNT/A-L in citrate plasma is increased. The background response to the control blank is higher than in the case of BoNT/A-L in LcA Hydrolysis Buffer (FIG. 9). This is due to the presence of naturally occurring proteases in blood plasma, which also cleave the peptide linkers. Of the several hundred substances in blood, some are coagulation factors, which in their active form are serine peptidases and which would undoubtedly interfere with protease-based assays for BoNT. For example factors Xa and IXa are capable of hydrolyzing an arginine-isoleucine bond, and factor XIa is capable of hydrolyzing an arginine-alanine bond, both of which are part of the BoNT/A recognition sequence on SNAP25. This higher background lowers the sensitivity of the assay for samples in citrate plasma.

V. Conclusions

Proof-of-principle has been shown for a rapid, sensitive luminescence assay for detecting the proteolytic activity of BoNT/A-L in microliter samples. In addition to detecting BoNT/A-L, the assay should also be effective for detecting the light chain of BoNT types C and E. With a little effort, the assay can be extended to other types of toxin by changing the protein coding region for the cutting and recognition sequence. For toxin types B, D, F and G a cDNA portion encoding human Synaptobrevin 2 (VAMP2) amino acids 1-102 could be cloned into pHA-2SL using suitable oligonucleotides. This would provide a single test for detecting the presence of any of the seven types of BoNT.

Key points about the assay:
1. The assay can be performed using a standard micro plate reader in about half an hour.
2. The assay is about 1000 times more sensitive than commercially available SNAPtide #521 [3].
3. The beads remain active for at least four months in buffer containing 30% sucrose when stored at −20 C.
4. The sensitivity of the assay depends on the use of full recognition sequences in the cleavable peptide.
5. The use of two cutting and recognition sequences in the cleavable peptide provides additional sensitivity.
6. The magnetic beads make the assay quick and easy to use.

Points 4 and 5 demonstrate novel key elements of the assay. With further development, the assay should be useful for rapidly detecting any of the types and subtypes of BoNT in blood serum.

Advantages of the Assay:
1. The use of luciferase rather than a fluorescence marker leads to extra amplification of the signal due to the enzymatic activity of the luciferase.
2. The use of luciferase rather than a fluorescence marker leads to a lowering of the background signal for the blank.
3. The use of magnetic beads provides a large surface area for the toxin to access the cleavable peptide.
4. The use of magnetic beads improves the speed of the assay and ease of use.
5. The use of two full cutting and recognition sequences in the cleavable peptide leads to greater sensitivity than when one cutting and recognition sequence is used.
6. The assay design allows for inclusion of cutting and recognition sequences that are susceptible to attack by BoNT types B, D, F and G in the cleavable peptide so that the presence of any of the types of BoNT could be tested at the same time.
7. The protein for the assay consisting of the HaloTag, the cleavable peptide and the luciferase marker can be produced cheaply in large amounts by bacterial expression.
8. The bacterial lysate can be used for coating the beads without the need for purification.
9. The beads remain active for at least four months when stored at −20 C in buffer containing 30% sucrose.

10. The assay can be used to detect BoNT/A in complex media such as blood serum.

Points 2, 5, 7, 8 and 10 have been demonstrated experimentally in this section. Points 1, 2, 4 and 5 distinguish the assay from previous assays.

Appendix A: Construction of PHA-1SL and PHA-2SL, and Expression of Fusion-Proteins Plasmids pET-30c(+) (Merck) and pGEM-luc (Promega) were digested using BamHI and XhoI enzymes in Buffer D (Promega), and the digestion products separated by gel electrophoresis. Gel electrophoresis was performed on 1% agarose stained with 0.5 µg ethidium bromide/ml. Bands at 5401 and 1698 base pairs were cut out from the gel, purified with Wizard SV Gel and PCR Clean-Up System (Promega) and ligated using T4 DNA ligase in 2× Flexi Ligase Buffer (Promega) to create pET-L.

Single Step (KRX) Competent $E.$ $coli$ cells (Promega) were transformed with the ligation product pET-L. After overnight growth on 1.5% agar with 30 µg kanamycin/ml, clones were picked out and grown in LB media with 30 µg kanamycin/ml. The plasmid was purified using the Miniprep System (Promega). The plasmid was digested with XhoI and BamHI restriction enzymes (Promega), and the products identified by gel electrophoresis. Expression of luciferase was induced by addition of Isopropyl β-D-1-thiogalactopyranoside (IPTG) and Rahmnose (final concentrations: 1 mM and 0.001% respectively). The presence of luciferase was detected by mixing 10 µl of culture with 25 µl Promega BrightGlo Assay in a white 96 well plate (Thermo Cliniplate), and measuring the luminescence in a PHERASTAR™ plus microplate reader (BMG labtech).

Human SNAP-25 protein coding region was derived from ORF Shuttle Clone AM393653 (OCAAo5051G0517D, Ima-Genes). DH10B $E.$ $coli$ with pENTR221 containing ORF Shuttle clone AM393653 was grown overnight in LB media with 30 µkanamycin/ml. The plasmid was purified using PureYield Plasmid Miniprep System (Promega).

For inserting one SNAP-25 sequences between the Kpn I and BamH I restriction sites of pET-L, pENTR221 with AM393653 was amplified by PCR with forward primer 5' GAC TGG TAC CAT GGA TGA AAA CCT AGA G 3' (SEQ ID NO:2) and reverse primer 5' AGT CGG ATC CCA CCA CTT CCC AGC ATC T 3' (SEQ ID NO:3) to provide the protein coding region for human SNAP-25 amino acids 146-206 with Kpn I and BamH I restriction sites on the 5' and 3' ends respectively.

For inserting two SNAP-25 sequences between the Kpn I and BamH I restriction sites of pET-L, pENTR221 with AM393653 was amplified by PCR with forward primer 5' GAC TGG TAC CAT GGA TGA AAA CCT AGA G 3' (SEQ ID NO:4) and reverse primer 5' CCC CAA GCT TAC CAC TTC CCA GCA TCT T 3' (SEQ ID NO:5), and with forward primer 5' GCC CAA GCT TAT GGA TGA AAA CCT AGA G 3' (SEQ ID NO:6) and reverse primer 5' AGT CGG ATC CCA CCA CTT CCC AGC ATC T 3' (SEQ ID NO:7) to provide the protein coding region for human SNAP-25 amino acids 146-206 with Kpn I and Hind III, and Hind III and BamH I restriction sites on the 5' and 3' ends respectively. These PCR products were digested with Hind III enzyme in Buffer B (Promega), purified by gel electrophoresis and Wizard SV Gel and PCR Clean-Up System, and ligated to form a DNA sequence encoding 2SNAP-25 sequences in series, with a Kpn I and BamH I restriction site at the 5' and 3' ends respectively.

Mixtures pET-L acceptor vector, and purified PCR products encoding one or two regions of SNAP-25 amino acids 146-206, were digested with KpnI and BamHI in Multicore buffer (Promega), purified by gel electrophoresis and Wizard SV Gel and PCR Clean-Up System, and ligated to form plasmids pET-1SL and pET-2SL respectively. The fusion-proteins encoded by these plasmids were expressed in KRX $E.$ $coli$ cells and purified via a His6 tag on a column of Ni-NTA Superflow (5 Prime).

To create pHA-1SL, pET-1SL was amplified by PCR with forward primer 5' AGT GGC GAT CGC CAA ATT CGA ACG CCA GCA CAT GGA CAG CCC AGA TCT GGG TAC C 3' (SEQ ID NO:8) and reverse primer 5' TAC GGT TTA AAC CAA TTT GGA CTT TCC GCC CTT CTT GGC CTT TAT GAG GAT CTC T 3' (SEQ ID NO:9) to provide DNA encoding protein coding region for human SNAP-25 amino acids 146-206 and luciferase with SgfI and PmeI restriction sites on the 5' and 3' ends respectively.

To create pHA-2SL, pET-2SL was amplified by PCR with forward primer 5' AGT GGC GAT CGC TAA ATT CGA ACG CCA GCA CAT GGA CAG CCC AGA TCT GGG TAC C 3' (SEQ ID NO:10) and reverse primer 5' TAC GGT TTA AAC CAA TTT GGA CTT TCC GCC CTT CTT GGC CTT TAT GAG GAT CTC T 3' (SEQ ID NO:11) to provide DNA encoding protein coding region for two sequences of human SNAP-25 amino acids 146-206 and luciferase with SgfI and PmeI restriction sites on the 5' and 3' ends respectively.

The PCR products were purified using the Wizard SV Gel and PCR Clean-Up System. The purified PCR products and pFN18A acceptor vector were digested with Flexi Enzyme Blend (SgfI and PmeI) in 5× Flexi Digest Buffer. After incubation for 30 minutes, the restriction enzymes in the digestion product of the pFN18A acceptor vector were inactivated by heating the reaction mixture to 65 C for 20 minutes. The digested PCR products were purified using the Wizard SV Gel and PCR Clean-Up System. The PCR products and pFN18A were ligated by incubation with T4 DNA ligase in 2× Flexi Ligase Buffer for one hour at room temperature before transforming KRX $E.$ $coli$ cells with the ligation products.

Fusion-proteins encoded by pHA-1SL and pHA-2SL were expressed in $E.$ $coli$ KRX cells. Cells were pelleted by centrifugation and resuspended in LEW buffer (50 mM $Na_2HPO_4$, 300 mM NaCl, pH 8.0) with 1 mg lysozyme/ml and a few crystals of DNase I. After incubation for 30 minutes at 4 C the suspension was centrifuged at 24,000 r.c.f. for 5 minutes. Fusion-proteins encoded by pHA-1SL or pHA-2SL were captured from the supernatant with HaloLink magnetic beads during 30 minutes incubation at room temperature with rotation at 10 r.p.m. Beads were washed several times with LEW buffer, resuspended in LEW buffer with 30% sucrose, and stored at −20 C.

Serial Dilution of BoNT/A-L

Serial dilutions of 100, 33, 10, 3.3, 1.0, 0.3, 0.1, 0.03, 0.01, 0.003, 0.001 and 0.0003 nM recombinant BoNT/A-L were made by mixing 47.4 µl 316 nM, or 47.4 µl previous dilution recombinant BoNT/A-L (Toxogen GmbH or List Biological Laboratories) in 102.6 µl citrate plasma or LcA Hydrolysis Buffer IGEPAL (20 mM HEPES, 0.5 mg/ml BSA, pH 8.2, 0.01% IGEPAL CA-620) in a Corning 96 well white solid NBS (Non Binding Surface) Microplate.

References

1. Woods J B (ed.): USAMRIID's MEDICAL MANAGEMENT OF BIOLOGICAL CASUALTIES HANDBOOK, 6th edn. Frederick: U. S. Army Medical Research Institute of Infectious Diseases; 2005.
2. Ferreira J L, Eliasberg S J, Harrison M A, Edmonds P: Detection of preformed type A botulinal toxin in hash brown potatoes by using the mouse bioasssay and a modified ELISA test. *Journal of Aoac International* 2001, 84(5):1460-1464.
3. CDC (ed.): Botulism in the United States, 1899-1996. Atlanta: Centres for Disease Control and Prevention; 1998.
4. Los G V, Encell L P, McDougall M G, Hartzell D D, Karassina N, Zimprich C, Wood M G, Learish R, Ohana R F, Urh M et al: HaloTag: A Novel Protein Labeling Technology for Cell Imaging and Protein Analysis. *ACS Chemical Biology* 2008, 3(6):373-382.
5. Breidenbach M A, Brunger A T: Substrate recognition strategy for botulinum neurotoxin serotype A. *Nature* 2004, 432(7019):925-929.
6. Poulain B, Popoff M, Molgo J: How do the Botulinum Neurotoxins block neurotransmitter release: from botulism to the molecular mechanism of action. *The Botulinum Journal* 2008, 1(1):14-87.
7. Dong M, Tepp W H, Johnson E A, Chapman E R: Using fluorescent sensors to detect botulinum neurotoxin activity in vitro and in living cells. *Molecular Biology of the Cell* 2004, 15:103a-103a.
8. Ruge D R, Dunning F M, Piazza T M, Molles B E, Adler M, Zeytin F N, Tucker W C: Detection of six serotypes of botulinum neurotoxin using fluorogenic reporters. *Analytical Biochemistry* 2011, 411(2):200-209.
9. Rodbard D: Statistical Estimation of Minimal Detectable Concentration (Sensitivity) for Radioligand Assays. *Analytical Biochemistry* 1978, 90(1):1-12.

A similar system to the Halo-Tag system (Promega) is available from New England biolabs, and can be used instead of the Halo-Tag system for the BoNT assay. SNAP tag (New England Biolabs) is a 20 kDa fusion protein (the Halo tag is 43 kDa) which covalently links to O-benzylguanine derivativese (see Antje Keppler, Susanne Gendreizig, Thomas Gronemeyer, Horst Pick, Horst Vogel and Kai Johnsson, *A general method for the covalent labeling of fusion proteins with small molecules in vivo*, nature biotechnology Vol 21, JANUARY 2003, 86-89.). The coding region of interest (in this case the SNAP25-luciferase, or the SNAP25-SNAP25-luciferase) can be cloned into the plasmid pSNAP-tag(T7)-2 for expression in *E. coli* (N9181S). The restriction map of such a vector is shown in the FIG. 13. A suitable magnetic bead for use with the SNAP tag, also provided by New England biolabs, is SNAP-Capture Magnetic Beads (catalogue # S9145S). As with the HaloLink beads from Promega, these beads are also suitable for use with cell lysates.

Example 2

Immobilization of the linker to a bead-like solid support was investigated using both affinity tag and covalent-like immobilization using the Halo Tag. Here is can be seen that immobilization with the affinity tags was inferior to covalent-like immobilization. Convenient handling of immobilized proteins was provided by using magnetic beads, but non-magnetic beads were also used in an automated centrifugal microfluidic device that was developed in parallel with this assay.

Affinity Tag Immobilization.

pET-1SL and pET-2SL. Human SNAP-25 protein coding region (Gen Bank # AM393653) was derived from ORF Shuttle Clone OCAAo5051G0517D (Source BioScience LifeSciences, Berlin, Germany). DH10B strain *E. coli* with pENTR221 containing ORF Shuttle clone AM393653 was grown overnight in Lysogeny broth (LB) media with 30 μg kanamycin/mL. The plasmid was purified using PureYield Plasmid Miniprep System (Promega).

For inserting one SNAP-25 sequences between the KpnI and BamHI restriction sites of pET-L, pENTR221 with AM393653 was amplified by PCR with forward primer 5' GAC TGG TAC CAT GGA TGA AAA CCT AGA G 3' (SEQ ID NO:12) and reverse primer 5' AGT CGG ATC CCA CCA CTT CCC AGC ATC T 3' (SEQ ID NO:13). This provided the protein coding region for human SNAP-25 amino acids 146-206 with KpnI and BamHI restriction sites on the 5' and 3' ends respectively.

For inserting two SNAP-25 sequences between the KpnI and BamHI restriction sites of pET-L, pENTR221 with AM393653 was amplified by PCR with forward primer 5' GAC TGG TAC CAT GGA TGA AAA CCT AGA G 3' (SEQ ID NO:14) and reverse primer 5' CCC AAG CTT ACC AC TTC CCA GCA TCT T 3' (SEQ ID NO:15), and with forward primer 5' GCC AAG CTT ATG GAT GAA AAC CT AGA G 3' (SEQ ID NO:16) and reverse primer 5' AGT CGG ATC CCA CCA CTT CCC AGC ATC T 3' (SEQ ID NO:17). This provided the protein coding region for human SNAP-25 amino acids 146-206 with KpnI and HindIII, and HindIII and BamHI restriction sites on the 5' and 3' ends respectively. These PCR products were digested with Hind III enzyme in Buffer B (Promega), purified by gel electrophoresis and ligated to form a DNA sequence encoding 2 SNAP-25 sequences in series, with a KpnI and BamHI restriction site at the 5' and 3' ends respectively.

Mixtures of pET-L and purified PCR products encoding one or two regions of SNAP-25 amino acids 146-206 were digested with KpnI and BamHI in Multicore buffer (Promega), purified by gel electrophoresis and ligated to form products called pET-1SL, shown schematically in FIG. 14 (*a*), and pET-2SL is shown in FIG. 14 (*b*). Plasmids were purified and digested with KpnI/XhoI. Plasmid pET-1SL digestion products had expected sizes of 5,342 and 1,910 bp, as indicated in the restriction map of FIG. 14 (*a*). For the case of pET-2SL, bands were found at 5,342 and 2,099 bp after KpnI/XhoI digestion, as indicated in the restriction map of FIG. 14 (*b*).

The presence of luciferase was detected by mixing 10 μL of cell culture with 25 μL BrightGlo Assay (Promega) on a white 96 well Cliniplate (Thermo Scientific), and measuring the luminescence. This was found to increase as the culture grew, indicating that the luciferase protein coding region was in the correct reading frame.

The fusion protein (ET-2SL), shown schematically in FIG. 15(*a*), provides both a polyhistidine tag and an S-Tag (combined tags denoted by HS) for immobilizing the polypeptide linker to beads or resin. Cell lysate containing ET-2SL was purified by Immobilized Metal Affinity Chromatography (IMAC) and then incubated for 30 minutes with 0-79 nM LC/A1 in LC/A Hydrolysis Buffer. An SDS-PAGE analysis of the response is shown in FIG. 15 (*b*). In the absence of LC/A1 a band at 79 kDa is visible, which is the expected size of ET-2SL. After incubation with LC/A1, the 79 kDa band disappeared and bands corresponding to cleavage products of 62 and 17 kDa appeared. These are the expected sizes of products after hydrolysis of the Gln(197)-Arg(198) peptide bond of SNAP-25 closest to the C terminal end of ET-2SL, as indicated in FIG. 15(*a*). With decreasing LC/A1 concentration, the intensity of the 79 kDa band reappeared and the intensity of bands for the cleavage products decreased. This is consistent with the cleavage rate being proportional to the concentration of LC/A1, which is expected for an enzymatic reaction. At LC/A1 concentrations of 25 and 79 nM, the 17 kDa cleavage product was replaced with one of 10 kDa. However, there was no corresponding cleavage product of 69 kDa visible, but only the 62 kDa product. This indicates that the Gln(197)-Arg (198) bond of the SNAP-25 closest to the C terminal of ET-2SL was cleaved at a higher rate than the one closest to the N terminal. At the higher LC/A concentrations, the 17 kDa fragment was cleaved, as shown by the faint band at 10 kDa.

Response with the Polyhistidine Tag.

Cell lysate containing ET-2SL was purified by IMAC and then incubated for 20 minutes with LC/A1 in LC/A Hydrolysis Buffer at concentrations in the range 100 to 100,000 pM, as shown in FIG. 15(*c*). The extent of cleavage by LC/A was determined by introducing NiNTA matrix suspended in 25 mM imidazole to the mixture in order to immobilize intact ET-2SL. After 20 minutes incubation, the matrix was removed, taking with it uncleaved ET-2SL, and leaving released luciferase to produce the luminescence signal shown in FIG. 15(*c*). It was found that 25 mM imidazole was required in the sample buffer to prevent weak interactions between luciferase and the Ni-NTA matrix due to naturally occurring histidine residues near the surface of luciferase (Conti, Franks et al. 1996). As shown in FIG. 15 (*c*), the LC/A1 concentration which produced half the total luminescence ($EC_{50}$) was at least 10,000 pM LC/A1. However, this response to LC/A1 was significantly higher than for HaloLink Magnetic Beads loaded with HA-2SL, shown for comparison in FIG. 15(*c*), with an $EC_{50}$ of approximately 1,000 pM LC/A1. In addition to lower sensitivity of the polyhistidine pull-down assay, the background signal was significantly higher than that of the HA-2SL assay.

Response with the S-Tag.

S-Protein agarose was incubated with lysate containing ET-SL, and the response to 0 and 1 nM LC/A1 was measured. The luminescence signal of the blank was approximately 80% of that of the luminescence signal of the analyte (data not shown). Stringent washing did not remove the high background signal, which was perhaps due to partial disintegration of the fragile S-protein agarose while shaking during incubation. To test this, beads with ET-2SL were immobilised in a column and the analyte was passing through the column. The response of ET-2SL on S-protein in a micro column is shown in FIG. 15 (*d*). Here it can be seen that the background is approximately 20% of that of the maximum luminescence value, confirming the suspicion that the high background was due to disintegration of beads. The response to 1 nM LC/A1 was greater with the S-tag than with the polyhistidine tag. However, the assay was difficult to perform and the maximum luminescence signal was relatively small. The higher signal and lower background of the ET-2SL assays compared to SNAPtide #521 were encouraging, but a more robust system of immobilization was required. This led to the use of the HaloTag, which provides a covalent-like linkage to beads via a chloroalkane linker immobilized onto the surface of a bead (Los, Encell et al. 2008).

Response with One SNAP-25 (16-206) Sequence.

Fusion protein HA-1S(16-206) was constructed by cloning DNA encoding human SNAP25 amino acids 146-206 and a firefly luciferase into the pFN-18A vector (Promega), to provide a HaloTag for immobilizing the polypeptide linker to HaloLink Magnetic Beads. Plasmid pHA-2S(16-206)L, shown schematically in FIG. 16(*a*), was constructed by amplifying the DNA sequence containing human SNAP-25 (GenBank # AM393653 from ORF Shuttle Clone OCAAo5051G0517D (Source BioScience LifeSciences, Berlin, Germany) with forward primer 5' ACT GGC GAT CGC GCG AAG GGC TGA CCA GTT GGC 3' (SEQ ID NO:18) and reverse primer 5' TGA CGA GCT CAC CAC TTC CCA GCA TCT TTG TTG C 3' (SEQ ID NO:19). This provided the protein coding region for human SNAP-25 amino acids 16-206 with SgfI and SacI restriction sites on the 5' and 3' ends respectively. pET-1SL was amplified by PCR with forward primer 5' GAT CGC TAG CGC CGA CGA CGA CGA CAA GGC CA 3' (SEQ ID NO:20) and reverse primer 5' TAG GGT TTA AAC GGC CTC GGA GGA TTA CAA TAG CTA AG 3' (SEQ ID NO:21) to provided a protein coding region for luciferase with SacI and PmeI restriction sites on the 5' and 3' ends respectively. The PCR products were digested with SacI, purified and ligated to form an insert consisting of SgfI-SNAP25(16-206)-SacI-luciferase-PmeI.

PCR products were purified using the Wizard SV Gel and PCR Clean-Up System (Promega). The purified PCR products and pFN18A acceptor vector (Promega) containing the HaloTag were digested with restriction enzymes SgfI and PmeI. After incubation for 30 minutes, the restriction enzymes were inactivated by heating the reaction mixture to 65 C for 20 minutes. The digested PCR products were purified using the Wizard SV Gel and PCR Clean-Up System. The PCR products and pFN18A were ligated for one hour at room temperature before transforming *E. coli* with the ligation product.

Cultures were grown at 37° C. with shaking at 180 r.p.m. to an OD600 of 0.8, and at 25° C. thereafter. Protein expression was induced when the OD600 reached 1-1.5, by addition of 0.1% L-Rhamnose and 1 mM Isopropyl β-D-1-thiogalactopyranoside. Cells were pelleted after overnight growth by centrifuging at 4,000 r.c.f. and stored at −80° C. or used immediately. Lysis was effected by resuspending cell pellets in HaloLink Bead Wash/Binding Buffer (100 mM Tris, 150 mM NaCl pH 7.6, 0.005% IGEPAL CA-630) with 1 mg/mL lysozyme and 10 μg/mL DNase I and 5 mM $MgCl_2$, followed by two freeze-thaw cycles. Lysate was clarified by centrifuging at 24,000 r.c.f. for 15 minutes. The response of HaloLink Magnetic Beads activated with HA-1S (16-206)L to LC/A1 is shown in FIG. 16(*c*). The data were fitted with a four parameter dose response curve. The LC/A1 concentration which produced half the total luminescence ($EC_{50}$) was 285±14 pM. A comparison of this assay with assays employing the shorter SNAP-25 sequences (amino acids 146-206) HA-1SL and HA-2SL is shown in FIG. 16(*d*). Four parameter fits to these data give $EC_{50}$ values of 10,110±275 pM and 948±50 pM for the assays using constructs HA-1SL and HA-2SL respectively. Thus the assay with the longer polypeptide, SNAP-25 amino acids 16-206, was comparable in sensitivity to that with two consecutive sequences of SNAP-25 (146-206). The construct with one SNAP-25 (146-206) provided an assay with considerably less sensitivity than these two.

Note on the Performance of the Assay with Halo Tag and Two SNAP-25(146-206).

HaloLink Magnetic Beads were treated with HA-2SL in batches and stored at −20° C. in buffer with 30% sucrose as a cryoprotectant, which was found to preserve the response to LC/A1. The effect of 10 to 80 minutes incubation on the response of two batches (A and B) of beads to LC/A Hydrolysis Buffer is shown in FIG. 17(*a*). This background response was due to release of luciferase from the beads by means other than hydrolysis of the SNAP25 polypeptide linker. The blank signal was different for the two batches, despite the beads having been prepared in the same way. A linear least squares fit to the data shows that in both cases the blank signal increased linearly with incubation time, and at different rates. This illustrates a level of variability in different batches, and the need for making a calibration curve for each batch.

The effect of 10 pM and 1 nM recombinant LC/A1 on batches of beads A and B respectively is shown in FIG. 17(b). The response is the difference between the luminescence of the analyte (10 pM or 1 nM LC/A1) and the blank, and is due to LC/A1 hydrolysis of the polypeptide linker. A linear least squares fit to the data for beads incubated with 10 pM LC/A1 shows a linear response as a function of incubation time. The initial rate of the response to 1 nM LC/A1 was about 20 times greater than for 10 pM, and the rate fell after 40 minutes incubation. However, the data suggest that extending the incubation time beyond 80 minutes would have resulted in a greater luminescence signal at both LC/A1 concentrations.

Storage of Activated Beads.

HaloLink Magnetic Beads activated with HA-2SL were suspended in buffer containing 30% sucrose and stored at −20° C. Beads stored at −20° C. were stable for at least 6 months. As lyophilisation of beads would be useful when refrigeration was not available, beads activated with HA-2SL were lyophilised in 3% mannitol. After rehydration, the response of the beads, FIG. 17(c), was similar to that for beads stored at −20° C. in 30% sucrose. This shows the utility of the bead assay for field work and easy transportation. However, for convenience beads were stored at −20° C., and thawed at room temperature immediately before use in all other experiments.

Response to Holotoxin.

BoNT/A, B and E. As shown in FIG. 18(a), HA-2SL activated HaloLink Magnetic Beads were responsive to LC/A1 and LC/E, with the response for LC/E being about 10% of that for LC/A1. The beads were also responsive to BoNT/A and BoNT/A complex in Jones Buffer, and to a lesser extent to BoNT/E and BoNT/E complex, also in Jones Buffer. As expected the assay was not responsive to BoNT/B, because the recognition and cleavage sites for LC/B are not present on SNAP-25.

Cell Cultures.

The HA-2SL magnetic beads were responsive to cultures of all *Clostridium botulinum* serotype A strains tested, as shown in FIG. 18(b). The cells were cultured in TPGY media (tryptone-peptone-glucose-yeast) and diluted 1:10 in Jones buffer. The strains tested were subtypes A1 (1028), A2 (Friedrichshain), A3 (Loch Maree), a recent food-borne botulism strain AX (Chemnitz), and bivalent strains A1, B (NCTC11199) and A2, F (REB 1750) (Kirchner, Kramer et al. 2010).

Dysport.

As shown in FIG. 18(c), HaloLink Magnetic beads with HA-2SL responded to 5 mouse $LD_{50}$ units Dysport (abobotulinumtoxin A) in Jones Buffer after 20 minutes incubation, and 2 units after 60 minutes incubation. In both cases the t statistic was well above the 0.01 significance level for a one tailed t test with 10 degrees of freedom (t=2.764). The larger blank signal for the case of 2 units compared for 5 units was because a different batch of beads was used. The response to 2 units Dysport was greater than for 5 units Dysport because of the longer incubation time (60 mins vs 20 mins).

New Protein Constructs.

Plasmids encoding three SNAP(146-206) and two and three SNAP-25(16-206) and that are currently being developed are shown schematically in FIG. 19. These plasmids will be used to investigate whether it is possible to improve the sensitivity of the luciferase release assay. The protein for the assay, HA-2SL, can be produced at low cost by expression in *E. coli*. The assay is currently being assessed for use in an automated centrifugal microfluidic system, which is being developed in parallel, and should make it useful for detecting BoNT/A threats in the field. With a little effort, the assay could be extended to other serotypes of toxin by changing the protein coding region for the cutting and recognition sequence. For detecting proteolytic activity of BoNT/B, D, F and G, sequences of human Synaptobrevin 2 (VAMP2) would replace the SNAP-25 sequences.

REFERENCES

Breidenbach, M. A. and A. T. Brunger (2004). "Substrate recognition strategy for botulinum neurotoxin serotype A." *Nature* 432(7019): 925-929.

CDC, Ed. (1998). *Botulism in the United States, 1899-1996.* Atlanta, Centres for Disease Control and Prevention.

Chen, S. and J. T. Barbieri (2006). "Unique substrate recognition by botulinum neurotoxins serotypes A and E." *Journal of Biological Chemistry* 281(16): 10906-10911.

Chen, S., C. Hall, et al. (2008). "Substrate recognition of VAMP-2 by botulinum neurotoxin B and tetanus neurotoxin." *Journal of Biological Chemistry* 283(30): 21153-21159.

Conti, E., N. P. Franks, et al. (1996). "Crystal structure of firefly luciferase throws light on a superfamily of adenylate-forming enzymes." *Structure* 4(3): 287-298.

Dong, M., W. H. Tepp, et al. (2004). "Using fluorescent sensors to detect botulinum neurotoxin activity in vitro and in living cells." *Molecular Biology of the Cell* 15: 103a-103a.

Drummond, A. J., B. Ashton, et al. (2010). Geneious Available from http://www.geneious.com.

Ferreira, J. L., S. J. Eliasberg, et al. (2001). "Detection of preformed type A botulinal toxin in hash brown potatoes by using the mouse bioassay and a modified ELISA test." *Journal of Aoac International* 84(5): 1460-1464.

Humeau, Y., F. Doussau, et al. (2000). "How botulinum and tetanus neurotoxins block neurotransmitter release." *Biochimie* 82(5): 427-446.

Kirchner, S., K. M. Kramer, et al. (2010). "Pentaplexed Quantitative Real-Time PCR Assay for the Simultaneous Detection and Quantification of Botulinum Neurotoxin-Producing Clostridia in Food and Clinical Samples." *Applied and Environmental Microbiology* 76(13): 4387-4395.

Los, G. V., L. P. Encell, et al. (2008). "HaloTag: A Novel Protein Labeling Technology for Cell Imaging and Protein Analysis." *ACS Chemical Biology* 3(6): 373-382.

Rodbard, D. (1978). "Statistical Estimation of Minimal Detectable Concentration (Sensitivity) for Radioligand Assays." *Analytical Biochemistry* 90(1): 1-12.

Ruge, D. R., F. M. Dunning, et al. (2011). "Detection of six serotypes of botulinum neurotoxin using fluorogenic reporters." *Analytical Biochemistry* 411(2): 200-209.

Schantz, E. J. and E. A. Johnson (1992). "Properties and Use of Botulinum Toxin and Other Microbial Neurotoxins in Medicine." *Microbiological Reviews* 56(1): 80-99.

Sikorra, S., T. Henke, et al. (2008). "Substrate recognition mechanism of VAMP/synaptobrevin-cleaving clostridial neurotoxins." *Journal of Biological Chemistry* 283(30): 21145-21152.

Vaidyanathan, V. V., K. Yoshino, et al. (1999). "Proteolysis of SNAP-25 isoforms by botulinum neurotoxin types A, C, and E: Domains and amino acid residues controlling the formation of enzyme-substrate complexes and cleavage." *Journal of Neurochemistry* 72(1): 327-337.

Woods, J. B., Ed. (2005). *USAMRIID's MEDICAL MANAGEMENT OF BIOLOGICAL CASUALTIES HANDBOOK*. Frederick, U. S. Army Medical Research Institute of Infectious Diseases.

---

The invention claimed is:

1. A method of determining the presence or amount of Botulinum toxin (BoNT) in a test sample, said method comprising the steps of:
   a) providing a support and a peptide for attachment thereto, said peptide comprising:
      an amino acid sequence susceptible to proteolytic cleavage by BoNT,
      an amino acid sequence corresponding to a reporter domain that codes for a fluorescent or bioluminescent polypeptide, and
      a Halo-tag suitable for attaching the peptide to said support,
   b) covalently attaching said peptide to said support via said Halo-tag,
   c) adding the test sample to be investigated for presence or amount of BoNT, and
   d) determining the luminescence signal of the fluorescent or bioluminescent polypeptide,
   wherein the amino acid sequence susceptible to proteolytic cleavage by BoNT comprises at least one set of amino acids selected from the group consisting of amino acids 16-206 of SNAP25, amino acids 146-202 of SNAP25, amino acids 152-201 of SNAP25 and amino acids 1-102 of VAMP2.

2. The method of claim 1, wherein the Botulinum toxin (BoNT) is of serotype A, C, or E.

3. The method of claim 2, wherein the Botulinum toxin (BoNT) is of serotype A.

4. The method of claim 1, wherein the amino acid sequence susceptible to proteolytic cleavage by BoNT comprises at least two sets of amino acids 146-206 of SNAP25.

5. The method of claim 1, wherein the SNAP25 is human SNAP25.

6. The method of claim 1, wherein the support is a bead.

7. The method of claim 6, wherein step c) comprises the step of removing the support and any uncleaved peptide.

8. The method of claim 6, wherein the support is a magnetic bead.

9. The method of claim 1, wherein the support is a microchip.

10. The method of claim 1, wherein said peptide of a) comprises: said Halo-tag, two sets of amino acids 152-201 of SNAP25 and said fluorescent or bioluminescent polypeptide in series.

11. The method of claim 1, wherein said peptide of a) comprises: said Halo-tag, amino acids 16-206 of SNAP25, and said fluorescent or bioluminescent polypeptide in series.

12. The method of claim 1, wherein the test sample to be investigated is blood serum.

13. The method of claim 1, wherein the fluorescent or bioluminescent polypeptide is firefly luciferase.

14. The method of claim 13, wherein the firefly luciferase is East European firefly luciferase (EC 1.13.12.7).

15. The method of claim 1, wherein the VAMP2 is human.

16. The method of claim 1, wherein the peptide a) comprises at least three sets of an amino acid sequence selected from the group consisting of: amino acids 16-206, 146-206, 146-202, and 152-201 of the human SNAP25 amino acid sequence (SEQ ID NO: 1) in series with said Halo-tag and said fluorescent or bioluminescent polypeptide.

17. A method of determining the presence or amount of Botulinum toxin (BoNT) in a test sample, said method comprising the steps of:
  a) providing a support and one or more peptides for attachment thereto, wherein said one or more peptides have the formula "TAG-X-REP" in which:
    X is an amino acid sequence susceptible to proteolytic cleavage by BoNT,
    REP is an amino acid sequence corresponding to a reporter domain that codes for a fluorescent or bioluminescent polypeptide, and
    TAG is a Halo-tag suitable for attaching the peptide to said support,
  b) covalently attaching said one or more peptides to said support via said Halo-tag,
  c) adding the test sample to be investigated for presence or amount of BoNT,
  d) determining the luminescence signal of the fluorescent or bioluminescent polypeptide, and
  e) correlating the luminescence signal determined in step d) with the presence and/or amount of BoNT in the test sample, wherein the amino acid sequence susceptible to proteolytic cleavage by BoNT consists of SEQ ID NO: 22 or
  wherein the amino acid sequence susceptible to proteolytic cleavage by BoNT comprises amino acids 28 to 90 of SEQ ID NO: 28.

18. The method of claim 17, wherein the amino acid sequence susceptible to proteolytic cleavage by BoNT consists of SEQ ID NO: 22.

19. The method of claim 17, wherein the amino acid sequence susceptible to proteolytic cleavage by BoNT comprises amino acids 28 to 90 of SEQ ID NO: 28.

* * * * *